US008058006B2

(12) United States Patent
Jonas

(10) Patent No.: US 8,058,006 B2
(45) Date of Patent: Nov. 15, 2011

(54) METHOD FOR OBTAINING AND INITIATING AMPLIFICATION OF A TARGET NUCLEIC ACID SEQUENCE

(75) Inventor: Vivian Jonas, Spring Valley, CA (US)

(73) Assignee: Gen-Probe Incorporated, San Diego, CA (US)

( * ) Notice: Subject to any disclaimer, the term of this patent is extended or adjusted under 35 U.S.C. 154(b) by 292 days.

(21) Appl. No.: 12/301,602

(22) PCT Filed: May 24, 2007

(86) PCT No.: PCT/US2007/069692
§ 371 (c)(1),
(2), (4) Date: Nov. 19, 2008

(87) PCT Pub. No.: WO2007/140279
PCT Pub. Date: Dec. 6, 2007

(65) Prior Publication Data
US 2009/0203007 A1 Aug. 13, 2009

Related U.S. Application Data

(60) Provisional application No. 60/803,127, filed on May 24, 2006.

(51) Int. Cl.
*C12Q 1/68* (2006.01)
*C12P 19/34* (2006.01)

(52) U.S. Cl. ...................................... 435/6.12; 435/91.2

(58) Field of Classification Search ............. 435/6, 91.2, 435/6.12
See application file for complete search history.

(56) References Cited

U.S. PATENT DOCUMENTS 5,703,217 A 12/1997 Mabilat et al.
5,908,744 A 6/1999 McAllister et al.
6,110,678 A 8/2000 Weisburg et al.
2002/0127569 A1 9/2002 Weisburg et al.
2004/0265864 A1* 12/2004 Mitsuhashi ...................... 435/6

FOREIGN PATENT DOCUMENTS

EP 1 566 437 A1 8/2005
WO 0244339 A1 6/2002
WO 2007106407 A1 9/2007

OTHER PUBLICATIONS

Database SRS [Online], Nov. 7, 2007, Accession No. FB087381, Abstract.
Kurabachew et al., "Sequence analysis in the 23S rDNA region of Mycobacterium tuberculosis and related species," J. Microbiol. Methods, 2003, 54:373-380, Elsevier Science B.V., UK.
Stone et al., "Comparison of Mycobacterium 23S rRNA Sequences by High-Temperature Reverse Transcription and PCR," Int J Syst Bacteriol., 1995, 456(4):811-819, International Union of Microbiological Societies, UK.
Verma et al., Development of a 23S rRNA-based PCR assay for the detection of mycobacteria, Indian J Biochem Biophys., 1994, 31:288-294, National Institute of Science Communication and Information Resources, CSIR, India.
Wharam et al., "Specific detection of DNA and RNA targets using a novel isothermal nucleic acid amplification assay based on the formation of a three-way junction structure," Nucl. Acids Res., 2001, 29(11 e54):1-8, Oxford University Press, UK.
PCT Search Report, International Application No. PCT/US07/069692, Feb. 29, 2008.
PCT Written Opinion, International Application No. PCT/US07/069692, Feb. 29, 2008.
PCT International Preliminary Report on Patentability, International Application No. PCT/US07/069692, Dec. 11, 2008.
European Office Action, European Patent Application No. 07797749.4, Jan. 5, 2011.

* cited by examiner

*Primary Examiner* — Kenneth R. Horlick
(74) *Attorney, Agent, or Firm* — Charles B. Cappellari

(57) ABSTRACT

The present invention relates to oligonucleotides useful for determining the presence of *Mycobacterium tuberculosis* complex organisms in a test sample. The oligonucleotides of the present invention may be incorporated into detection probes, helper probes, capture probes and amplification oligonucleotides, and used in various combinations thereof.

16 Claims, No Drawings

SEQUENCE LISTING

<160> NUMBER OF SEQ ID NOS: 33

<210> SEQ ID NO 1
<211> LENGTH: 23
<212> TYPE: DNA
<213> ORGANISM: Artificial
<220> FEATURE:
<223> OTHER INFORMATION: Mycobacterium tuberculosis complex

<400> SEQUENCE: 1
ggaggatatg tctcagcgct acc                23

<210> SEQ ID NO 2
<211> LENGTH: 23
<212> TYPE: RNA
<213> ORGANISM: Artificial
<220> FEATURE:
<223> OTHER INFORMATION: Mycobacterium tuberculosis complex

<400> SEQUENCE: 2
ggaggauaug ucucagcgcu acc                23

<210> SEQ ID NO 3
<211> LENGTH: 23
<212> TYPE: DNA
<213> ORGANISM: Artificial
<220> FEATURE:
<223> OTHER INFORMATION: Mycobacterium tuberculosis complex

<400> SEQUENCE: 3
ggtagcgctg agacatatcc tcc                23

<210> SEQ ID NO 4
<211> LENGTH: 23
<212> TYPE: RNA
<213> ORGANISM: Artificial
<220> FEATURE:
<223> OTHER INFORMATION: Mycobacterium tuberculosis complex antisense
      RNA

<400> SEQUENCE: 4
gguagcgcug agacauaucc ucc                23

<210> SEQ ID NO 5
<211> LENGTH: 38
<212> TYPE: DNA
<213> ORGANISM: Artificial
<220> FEATURE:
<223> OTHER INFORMATION: Mycobacterium tuberculosis complex

<400> SEQUENCE: 5
cggctgagag gcagtacaga aagtgtcgtg gttagcgg                38

<210> SEQ ID NO 6
<211> LENGTH: 38
<212> TYPE: RNA
<213> ORGANISM: Artificial
<220> FEATURE:
<223> OTHER INFORMATION: Mycobacterium tuberculosis complex

<400> SEQUENCE: 6
cggcugagag gcaguacaga aagugucgug guuagcgg                38

<210> SEQ ID NO 7
<211> LENGTH: 38
<212> TYPE: DNA
<213> ORGANISM: Artificial
<220> FEATURE:
<223> OTHER INFORMATION: Mycobacterium tuberculosis complex

<400> SEQUENCE: 7
ccgctaacca cgacactttc tgtactgcct ctcagccg        38

<210> SEQ ID NO 8
<211> LENGTH: 38
<212> TYPE: RNA
<213> ORGANISM: Artificial
<220> FEATURE:
<223> OTHER INFORMATION: Mycobacterium tuberculosis complex antisense
      RNA

<400> SEQUENCE: 8
ccgcuaacca cgacacuuuc uguacugccu cucagccg        38

<210> SEQ ID NO 9
<211> LENGTH: 36
<212> TYPE: DNA
<213> ORGANISM: Artificial
<220> FEATURE:
<223> OTHER INFORMATION: Mycobacterium tuberculosis complex

<400> SEQUENCE: 9
gggtaaccgg gtaggggttg tgtgtgcggg gttgtg        36

<210> SEQ ID NO 10
<211> LENGTH: 36
<212> TYPE: RNA
<213> ORGANISM: Artificial
<220> FEATURE:
<223> OTHER INFORMATION: Mycobacterium tuberculosis complex

<400> SEQUENCE: 10
ggguaaccgg guagggguug ugugugcggg guugug        36

<210> SEQ ID NO 11
<211> LENGTH: 36
<212> TYPE: DNA
<213> ORGANISM: Artificial
<220> FEATURE:
<223> OTHER INFORMATION: Mycobacterium tuberculosis complex

<400> SEQUENCE: 11
cacaaccccg cacacacaac ccctacccgg ttaccc        36

<210> SEQ ID NO 12
<211> LENGTH: 36
<212> TYPE: RNA
<213> ORGANISM: Artificial
<220> FEATURE:
<223> OTHER INFORMATION: Mycobacterium tuberculosis complex antisense
      RNA

<400> SEQUENCE: 12
cacaaccccg cacacacaac cccuacccgg uuaccc        36

<210> SEQ ID NO 13
<211> LENGTH: 31
<212> TYPE: DNA
<213> ORGANISM: Artificial
<220> FEATURE:
<223> OTHER INFORMATION: Mycobacterium tuberculosis complex

<400> SEQUENCE: 13
cggaatcaca attgttttct cctcctacgg g                               31

<210> SEQ ID NO 14
<211> LENGTH: 31
<212> TYPE: RNA
<213> ORGANISM: Artificial
<220> FEATURE:
<223> OTHER INFORMATION: Mycobacterium tuberculosis complex antisense
      RNA

<400> SEQUENCE: 14
cggaaucaca auuguuuucu ccuccuacgg g                               31

<210> SEQ ID NO 15
<211> LENGTH: 31
<212> TYPE: DNA
<213> ORGANISM: Artificial
<220> FEATURE:
<223> OTHER INFORMATION: Mycobacterium tuberculosis complex

<400> SEQUENCE: 15
cccgtaggag gagaaaacaa ttgtgattcc g                               31

<210> SEQ ID NO 16
<211> LENGTH: 31
<212> TYPE: RNA
<213> ORGANISM: Artificial
<220> FEATURE:
<223> OTHER INFORMATION: Mycobacterium tuberculosis complex

<400> SEQUENCE: 16
cccguaggag gagaaaacaa uugugauucc g                               31

<210> SEQ ID NO 17
<211> LENGTH: 24
<212> TYPE: DNA
<213> ORGANISM: Artificial
<220> FEATURE:
<223> OTHER INFORMATION: Mycobacterium tuberculosis complex

<400> SEQUENCE: 17
ggaatcacaa ttgttttctc ctcc                                       24

<210> SEQ ID NO 18
<211> LENGTH: 24
<212> TYPE: RNA
<213> ORGANISM: Artificial
<220> FEATURE:
<223> OTHER INFORMATION: Mycobacterium tuberculosis complex antisense
      RNA

<400> SEQUENCE: 18
ggaaucacaa uuguuuucuc cucc                                       24

<210> SEQ ID NO 19
<211> LENGTH: 24
<212> TYPE: DNA
<213> ORGANISM: Artificial
<220> FEATURE:
<223> OTHER INFORMATION: Mycobacterium tuberculosis complex

<400> SEQUENCE: 19
ggaggagaaa acaattgtga ttcc                                       24

```
<210> SEQ ID NO 20
<211> LENGTH: 24
<212> TYPE: RNA
<213> ORGANISM: Artificial
<220> FEATURE:
<223> OTHER INFORMATION: Mycobacterium tuberculosis complex

<400> SEQUENCE: 20
ggaggagaaa acaauuguga uucc                                          24

<210> SEQ ID NO 21
<211> LENGTH: 20
<212> TYPE: DNA
<213> ORGANISM: Artificial
<220> FEATURE:
<223> OTHER INFORMATION: Mycobacterium tuberculosis complex

<400> SEQUENCE: 21
ccaggccact tccgctaacc                                               20

<210> SEQ ID NO 22
<211> LENGTH: 20
<212> TYPE: RNA
<213> ORGANISM: Artificial
<220> FEATURE:
<223> OTHER INFORMATION: Mycobacterium tuberculosis complex antisense
      RNA

<400> SEQUENCE: 22
ccaggccacu uccgcuaacc                                               20

<210> SEQ ID NO 23
<211> LENGTH: 20
<212> TYPE: DNA
<213> ORGANISM: Artificial
<220> FEATURE:
<223> OTHER INFORMATION: Mycobacterium tuberculosis complex

<400> SEQUENCE: 23
ggttagcgga agtggcctgg                                               20

<210> SEQ ID NO 24
<211> LENGTH: 20
<212> TYPE: RNA
<213> ORGANISM: Artificial
<220> FEATURE:
<223> OTHER INFORMATION: Mycobacterium tuberculosis complex

<400> SEQUENCE: 24
gguuagcgga aguggccugg                                               20

<210> SEQ ID NO 25
<211> LENGTH: 24
<212> TYPE: DNA
<213> ORGANISM: Artificial
<220> FEATURE:
<223> OTHER INFORMATION: Mycobacterium tuberculosis complex

<400> SEQUENCE: 25
cgcggaacag gctaaaccgc acgc                                          24

<210> SEQ ID NO 26
<211> LENGTH: 24
<212> TYPE: RNA
<213> ORGANISM: Artificial
<220> FEATURE:
<223> OTHER INFORMATION: Mycobacterium tuberculosis complex
```

-continued

<400> SEQUENCE: 26
cgcggaacag gcuaaaccgc acgc                                                24

<210> SEQ ID NO 27
<211> LENGTH: 24
<212> TYPE: DNA
<213> ORGANISM: Artificial
<220> FEATURE:
<223> OTHER INFORMATION: Mycobacterium tuberculosis complex

<400> SEQUENCE: 27
gcgtgcggtt tagcctgttc cgcg                                                24

<210> SEQ ID NO 28
<211> LENGTH: 24
<212> TYPE: RNA
<213> ORGANISM: Artificial
<220> FEATURE:
<223> OTHER INFORMATION: Mycobacterium tuberculosis complex antisense
      RNA

<400> SEQUENCE: 28
gcgugcgguu uagccuguuc cgcg                                                24

<210> SEQ ID NO 29
<211> LENGTH: 27
<212> TYPE: DNA
<213> ORGANISM: Artificial
<220> FEATURE:
<223> OTHER INFORMATION: Promoter

<400> SEQUENCE: 29
aatttaatac gactcactat agggaga                                             27

<210> SEQ ID NO 30
<211> LENGTH: 33
<212> TYPE: DNA
<213> ORGANISM: Artificial
<220> FEATURE:
<223> OTHER INFORMATION: Immobilized probe binding region of a capture
      probe

<400> SEQUENCE: 30
tttaaaaaaa aaaaaaaaaa aaaaaaaaaa aaa                                      33

<210> SEQ ID NO 31
<211> LENGTH: 57
<212> TYPE: DNA
<213> ORGANISM: Artificial
<220> FEATURE:
<223> OTHER INFORMATION: Mycobacterium tuberculosis complex capture
      probe
<220> FEATURE:
<221> NAME/KEY: misc_feature
<222> LOCATION: (1)..(24)
<223> OTHER INFORMATION: 2'-O-methylribonucleotides

<400> SEQUENCE: 31
ggaaucacaa uuguuuucuc cucctttaaa aaaaaaaaaa aaaaaaaaa aaaaaaa             57

<210> SEQ ID NO 32
<211> LENGTH: 24
<212> TYPE: RNA
<213> ORGANISM: Artificial
<220> FEATURE:
<223> OTHER INFORMATION: Mycobacterium tuberculosis complex antisense
      RNA

```
-continued

<220> FEATURE:
<221> NAME/KEY: misc_feature
<222> LOCATION: (1)..(24)
<223> OTHER INFORMATION: 2'-O-methylribonucleotides

<400> SEQUENCE: 32
ggaaucacaa uuguuucuc cucc                                            24

<210> SEQ ID NO 33
<211> LENGTH: 47
<212> TYPE: DNA
<213> ORGANISM: Artificial
<220> FEATURE:
<223> OTHER INFORMATION: Mycobacterium tuberculosis complex
      promoter-primer

<400> SEQUENCE: 33
aatttaatac gactcactat agggagacca ggccacttcc gctaacc                  47
```

METHOD FOR OBTAINING AND INITIATING AMPLIFICATION OF A TARGET NUCLEIC ACID SEQUENCE

CROSS-REFERENCE TO RELATED APPLICATIONS

This application is the National Stage of International Application No. PCT/US2007/069692, filed May 24, 2007, which claims the benefit of U.S. Provisional Application No. 60/803,127, filed May 24, 2006, the contents of each of which applications are hereby incorporated by reference herein.

FIELD OF THE INVENTION

The present invention relates to detection probes, helper probes, capture probes, amplification oligonucleotides, methods, and kits useful for determining the presence of *Mycobacterium tuberculosis* complex ("TB complex") organisms in a test sample. In addition to *M. tuberculosis*, the TB complex includes *M. africanum, M. bovis, M. bovis* BCG, *M. microti*.

BACKGROUND OF THE INVENTION

Tuberculosis ("TB") is a bacterial infection caused by members of the TB complex. Transmission occurs when a person with active pulmonary TB coughs, sneezes or spits, releasing a contaminated aerosol into the air. Inhalation of the released bacteria is the most common mode of infection. Highly infectious individuals are capable of transmitting the disease to 10 to 15 persons a year. While approximately one third of the world's population is infected with TB bacteria, the majority are asymptomatic latent TB infections ("LTBI"). Of the LTBI cases, one in ten will progress to active TB infection which, left untreated, have a 50% mortality rate. Persons lacking a competent immune system (i.e., children) or who are immuno-compromised (i.e., substance abuse, immunosuppresive drugs, HIV/AIDS, diabetes, kidney failure, etc.) are most at risk.

The World Health Organization declared TB a global health emergency in 1993. With close to 9 million new cases and 2 million TB-related deaths each year, this emergency is fueled by HIV and the growing threat of multi-drug resistant ("MDR-TB"). There are nearly 300,000 new cases of MDR-TB each year and over 50 million people are latently infected with MDR strains of TB. Persons co-infected with HIV and TB are most susceptible to active TB disease. It is recognized that the key to controlling the spread of TB is rapid and accurate diagnosis. TB diagnostics can be used not only in the diagnosis of symptomatic patients, but also in therapeutic drug monitoring. Thus, a need exists for a sensitive assay that is specific for the TB complex organisms, and which minimizes the potential for forming potentially contaminating aerosols that put technologists at risk.

SUMMARY OF THE INVENTION

The present invention responds to this need by providing a sensitive assay that is specific for members of the TB complex. This assay features oligonucleotides that are useful for determining whether a TB complex organism is present in a test sample (e.g., a sputum, bronchoalveolar lavage or pleural fluid sample). The featured oligonucleotides may be contained in detection probes, helper probes, capture probes and/or amplification oligonucleotides that are useful for detecting, immobilizing and/or amplifying TB complex target nucleic acid present in a test sample.

In one aspect of the invention, detection probes are provided that preferentially hybridize to a target sequence contained in a target nucleic acid derived from the 23S ribosomal RNA ("rRNA") or ribosomal DNA ("rDNA") of any of the TB complex organisms to form a detectable probe:target hybrid that indicates the presence of at least one TB complex organism in a test sample. Preferred detection probes have a target binding region that comprises at least 12, 13, 14 or 15 of 15 contiguous bases of a reference sequence selected from the group consisting of:

SEQ ID NO: 1    ggaggatatgtctcagcgctacc,

SEQ ID NO: 2    ggaggauaugucucagcgcuacc,

SEQ ID NO: 3    ggtagcgctgagacatatcctcc, and

SEQ ID NO: 4    gguagcgcugagacauauccucc.

Detection probes according to the present invention preferentially hybridize to TB complex-derived nucleic acid and not to nucleic acid derived from non-TB complex organisms present in a test sample under stringent hybridization conditions. In particular, the detection probes of the present invention preferentially hybridize to TB complex-derived nucleic acid and not to nucleic acid derived from *Mycobacterium celatum*, which is considered to be the most closely related organism to the TB complex organisms. For testing purposes, *M. celatum* can be obtained from the American Type Culture Collection in Manassas, Va. (ATCC No. 51130).

A detection probe of the present invention may have a target binding region of any length suitable to achieve the desired selectivity and specificity for TB complex-derived nucleic acid. The base sequence of the target binding region is preferably between 12, 13, 14 or 15 and 35 bases in length, and more preferably between 15 and 25 bases in length. The base sequence of the detection probe is preferably up to 15, 20, 25, 30, 35, 40, 50 or 100 bases in length. Preferably, the target binding region of the detection probe comprises, overlaps with, consists essentially of, substantially corresponds to, consists of, or is contained within the reference sequence. More preferably, the base sequence of the detection probe consists essentially of, substantially corresponds to, consists of, or is contained within the reference sequence.

The target binding region may consist of deoxyribonucleic acid (DNA), ribonucleic acid (RNA), a combination DNA and RNA, or it may be, in whole or in part, a nucleic acid analog having, for example, a modified backbone (e.g., a peptide nucleic acid), a modified sugar moiety (e.g., 2'-O-methyl ribose substitution), a base anolog (e.g., inosine), or a known derivative of a purine or pyrimidine base (e.g., deaza- or aza-purines and deaza- or aza-pyrimidines). The target binding region may additionally include molecules that do not hydrogen bond to adenine, cytosine, guanine, thymine or uracil, provided such molecules do not interfere with the ability of the detection probe to selectively and specifically bind to nucleic acid derived from TB complex organisms in the test sample. Examples of such molecules include abasic nucleotides and universal base analogues, such as 5-nitroindole, provided such molecules do not significantly affect duplex stability, See, e.g., Guo et al., "Artificial Mismatch Hybridization," U.S. Pat. No. 5,780,233, the contents of which are hereby incorporated by reference herein.

A detection probe of the present invention may include one or more base sequences in addition to the base sequence of the target binding region which do not stably bind to nucleic acid derived from any of the TB complex organisms under stringent hybridization conditions. An additional base sequence may be comprised of any desired base sequence, so long as it does not stably bind to nucleic acid derived from any of the TB complex organisms under stringent hybridization conditions or prevent stable hybridization of the probe to the target nucleic acid. By way of example, an additional base sequence may constitute an immobilized probe binding region of a capture probe, where the immobilized probe binding region is comprised of, for example, a 3' poly dA (adenine) region which hybridizes under assay conditions to a 5' poly dT (thymine) region of a polynucleotide bound directly or indirectly to a solid support. An additional base sequence might also be a 5' sequence recognized by a RNA polymerase or which enhances initiation or elongation by an RNA polymerase (e.g., a T7 promoter). More than one additional base sequence may be included if the first sequence is incorporated into, for example, a self-hybridizing probe (i.e., a probe having distinct base regions capable of hybridizing to each other in the absence of a target sequence under the conditions of an assay), such as a "molecular beacon" probe. Molecular beacons are disclosed by Tyagi et al., "Detectably Labeled Dual Conformation Oligonucleotide Probes, Assays and Kits," U.S. Pat. No. 5,925,517, the contents of which are hereby incorporated by reference herein. A molecular beacon includes a target binding region which is bounded by or overlaps with two base sequences having regions, referred to as "stems" or "arms," which are at least partially complementary to each other. A more detailed description of molecular beacons is provided infra in the section entitled "Detection Probes to Ribosomal Nucleic Acid of TB Complex Organisms." An additional base sequence may be joined directly to the target binding region or, for example, by means of a non-nucleotide linker (e.g., polyethylene glycol or an abasic region).

While not required, detection probes of the present invention preferably include at least one detectable label or group of interacting labels. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester (AE), preferably 4-(2-succinimidyloxycarbonyl ethyl)-phenyl-10-methylacridinium-9-carboxylate fluorosulfonate (hereinafter referred to as "standard AE"). Groups of interacting labels useful with a probe pair or a self-hybridizing probe include, but are not limited to, enzyme/substrate, enzyme/cofactor, luminescent/quencher, luminescent/adduct, dye dimers and Förrester energy transfer pairs. See Morrison, "Competitive Homogeneous Assay," U.S. Pat. No. 5,928,862 (bimolecular probes), the contents of which are hereby incorporated by reference herein; see also Tyagi et al., U.S. Pat. No. 5,925,517 (unimolecular probes). An interacting luminescent/quencher pair, such as fluoroscein and DABCYL, is particularly preferred.

The invention also contemplates compositions comprising stable nucleic acid duplexes formed between any of the above-described detection probes and the target nucleic acids for the probes under stringent hybridization conditions.

In a further aspect, the present invention contemplates probe mixes that are useful for determining whether a TB complex organism is present in a test sample. The probe mix may comprise, for example, one of the above-described TB complex detection probes and at least one helper probe that stably binds, under stringent hybridization conditions, to a target sequence contained in a target nucleic acid derived from the 23S rRNA or rDNA of any of the TB complex organisms and has a base sequence comprising at least 12, 13, 14 or 15 of 15 contiguous bases of a reference sequence selected from the group consisting of:

```
SEQ ID NO: 5
cggctgagaggcagtacagaaagtgtcgtggttagcgg,

SEQ ID NO: 6
cggcugagaggcaguacagaaagugucgugguuagcgg,

SEQ ID NO: 7
ccgctaaccacgacactttctgtactgcctctcagccg,

SEQ ID NO: 8
ccgcuaaccacgacacuuucguacugccucucagccg,

SEQ ID NO: 9
gggtaaccgggtaggggttgtgtgtgcggggttgtg,

SEQ ID NO: 10
ggguaaccggguaggggguugugugugcggguugug,

SEQ ID NO: 11
cacaacccgcacacacaaccctacccggttaccc,
and

SEQ ID NO: 12
cacaacccgcacacacaacccuacccgguuaccc.
```

A helper probe according to the present invention need not exhibit specificity for the target sequence in a test sample. The base sequences of preferred helper probes are preferably between 12, 13, 14 or 15 and 25, 30, 35, 40 or 50 bases in length. Preferably, the base sequence of a helper probe comprises, overlaps with, consists essentially of, substantially corresponds to, consists of, or is contained within the reference sequence. More preferably, the base sequence of the helper probe consists essentially of, substantially corresponds to, consists of, or is contained within the reference sequence.

The invention also contemplates compositions comprising stable nucleic acid duplexes formed between any of the above-described detection probes and/or helper probes and the target nucleic acids for the probes under stringent hybridization conditions.

In another aspect of the present invention, a capture probe is provided for isolating and purifying a 23S rRNA or rDNA target nucleic acid derived from a TB complex organism present in a test sample. The capture probe is up to 100 bases in length and includes a target binding region that stably binds to a target sequence contained in the TB complex-derived target nucleic acid under assay conditions and which comprises, overlaps with, consists essentially of, substantially corresponds to, consists of, or is contained within and includes an at least 12, 13, 14 or 15 of 15 contiguous base region of a reference sequence selected from the group consisting of:

```
SEQ ID NO: 13    cggaatcacaattgttttctcctcctacggg,

SEQ ID NO: 14    cggaaucacaauuguuuucuccuccuacggg,

SEQ ID NO: 15    cccgtaggaggagaaaacaattgtgattccg,

SEQ ID NO: 16    cccguaggaggagaaaacaauugugauuccg,
```

-continued

SEQ ID NO: 17    ggaatcacaattgttttctcctcc,

SEQ ID NO: 18    ggaaucacaauuguuuucuccucc,

SEQ ID NO: 19    ggaggagaaaacaattgtgattcc,
and

SEQ ID NO: 20    ggaggagaaaacaauugugauucc.

The base sequence of the target binding region of a capture probe according to the present invention is preferably up to 20, 25, 30, 35 or 40 bases in length. More preferably, the target binding region of the capture probe comprises, consists essentially of, substantially corresponds to, consists of, or is contained within the reference sequence.

Capture probes of the present invention may be immobilized on a solid support by means of ligand-ligate binding pairs, such as avidin-biotin linkages, but preferably include an immobilized probe binding region, as defined infra. The immobilized probe binding region of the preferred capture probes is comprised of any base sequence capable of stably hybridizing under assay conditions to an oligonucleotide that is bound to a solid support present in a test sample. Preferably, the immobilized probe binding region is a poly dA, homopolymer tail located at the 3' end of the capture probe. In this embodiment, oligonucleotides bound to the solid support would include 5' poly dT tails of sufficient length to stably bind to the poly dA tails of the capture probes under assay conditions. In a preferred embodiment, the immobilized probe binding region includes a poly dA tail which is about 30 adenines in length, and the capture probe includes a spacer region which is about 3 thymines in length for joining together the target binding region and the immobilized probe binding region.

The present invention also features amplification oligonucleotides useful for determining the presence of TB complex organisms in an amplification assay. In a preferred embodiment, at least one amplification oligonucleotide for amplifying a target region contained in a 23S rRNA or rDNA target nucleic acid derived from any TB complex organism is provided, where the amplification oligonucleotide is a first amplification oligonucleotide having a target binding region that stably binds, under amplification conditions, to a target sequence contained in the target nucleic acid or its complement and has a base sequence that comprises at least 12, 13, 14 or 15 of 15 contiguous bases of a sequence selected from the group consisting of:

SEQ ID NO: 21    cggaatcacaattgttttctcctcctacggg,

SEQ ID NO: 22    cggaaucacaauuguuuucuccuccuacggg,

SEQ ID NO: 23    cccgtaggaggagaaaacaattgtgattccg,
and

SEQ ID NO: 24    cccguaggaggagaaaacaauugugauuccg.

In another preferred embodiment, the amplification oligonucleotide for amplifying TB complex-derived nucleic acid is a second amplification oligonucleotide having a target binding region that stably binds, under amplification conditions, to a target sequence contained in the target nucleic acid or its complement and has abase sequence that comprises at least 12, 13, 14 or 15 of 15 contiguous bases of a sequence selected from the group consisting of:

SEQ ID NO: 25    ggaatcacaattgttttctcctcc,

SEQ ID NO: 26    ggaaucacaauuguuuucuccucc,

-continued

SEQ ID NO: 27    ggaggagaaaacaattgtgattcc,
and

SEQ ID NO: 28    ggaggagaaaacaauugugauucc.

Amplification oligonucleotides of the present invention have a target binding region that is preferably from 12, 13, 14 or 15 to 20, 25, 30, 35 or 40 bases in length. The target binding region of the amplification oligonucleotide preferably comprises, overlaps with, consists essentially of, substantially corresponds to, consists of, or is contained within the reference sequence. The amplification oligonucleotide optionally includes a 5' sequence which is recognized by a RNA polymerase or which enhances initiation or elongation by RNA polymerase. The T7 promoter sequence of SEQ ID NO:29: aatttaatacgactcactatagggaga is preferred, although other promoter sequences may be employed.

Amplification oligonucleotides of the present invention can be employed in sets of at least two amplification oligonucleotides, and preferably include an embodiment of each of the first and second amplification oligonucleotides described above. Generally, the set of amplification oligonucleotides will include at least one each of a sense and an antisense amplification oligonucleotide, although a plurality of the same sense primers may be used. At least one member of the set of amplification oligonucleotides preferably includes a 5' sequence which is recognized by an RNA polymerase or which enhances initiation or elongation by an RNA polymerase (e.g., a T7 promoter sequence). It is not a requirement of the present invention that each of the sense and antisense amplification oligonucleotides be capable of extension in the presence of a polymerase. See, e.g., Becker et al., "Single-Primer Nucleic Acid Amplification Methods," U.S. Patent Application Publication No. US 2006-0046265 A1, the contents of which are hereby incorporated by reference herein.

The invention additionally contemplates compositions comprising stable nucleic acid duplexes formed between any of the above-described amplification oligonucleotides and the target nucleic acid or its complement under amplification conditions.

The present invention further features methods for determining whether any TB-complex organisms are present in a test sample. In certain embodiments, the invention provides methods for determining whether any TB complex organisms are present in a test sample, where such methods comprise the steps of: (a) contacting the test sample with one of the above-described detection probes for detecting TB complex organisms under conditions permitting the probe to preferentially hybridize to TB complex-derived nucleic acid, thereby forming a probe:target hybrid stable for detection; and (b) determining whether the hybrid is present in the test sample as an indication of the presence or absence of any TB complex organisms in the test sample. This method may further include the step of quantifying the amount of hybrid present in the test sample as a means for estimating the amount of TB complex organisms present in the test sample. Numerous methods are known in the art approximating the number of organisms in a sample. See, e.g., Wittwer et al., "PCR Method for Nucleic Acid Quantification Utilizing Second or Third Order Rate Constants," U.S. Pat. No. 6,232,079; Sagner et al., "Method for the Efficiency-Corrected Real-Time Quantification of Nucleic Acids," U.S. Pat. No. 6,691,041; McMillan et al., "Methods for Quantitative Analysis of a Nucleic Acid Amplification Reaction," U.S. Pat. No. 6,911,327; and Chismar et al., "Method and Algorithm for Quantifying Polynucleotides," U.S. Patent Application Publication No. US 2006-0292619 A1 (the contents of each of the foregoing references is hereby incorporated by reference herein).

The methods for determining whether any TB complex organisms are present in a test sample, or the amount of any TB complex organisms present in a test sample, may further include the step of contacting the test sample with at least one of the above-describe helper probes for facilitating hybridization of the detection probe to a target sequence, and/or at least one of the above-described capture probes for isolating and purifying a TB complex-derived nucleic acid containing the target sequence or its complement, and/or at least one of the above-described amplification oligonucleotides appropriate for amplifying a region of TB complex-derived nucleic acid containing the target sequence or its complement, as desired.

The invention also contemplates kits for determining whether any TB complex organisms are present in a test sample. These kits include at least one of the above-described detection probes specific for a target sequence contained in a TB complex-derived nucleic acid and optionally include written instructions for determining the presence or amount of any TB complex organisms in a test sample. The kits may further include at least one of the above-described helper probes for aiding hybridization of the detection probe to the target sequence, and/or at least one of the above-described capture probes for separating a TB complex-derived nucleic acid containing the target sequence or its complement from other components of the test sample prior to amplifying or directly detecting the target nucleic acid, and/or at least one of the above-described amplification oligonucleotides appropriate for amplifying a region of TB complex-derived nucleic acid containing the target sequence or its complement, as desired.

In yet another aspect of the present invention, a method is provided for obtaining and initiating amplification of a target nucleic acid sequence which includes the following steps: a) exposing a sample to a lytic composition and conditions for a period of time sufficient to kill and lyse a difficult to lyse an organism, such as a mycobacterial organism (e.g., TB complex organism), thereby releasing a target nucleic acid into the sample, the lytic composition comprising a detergent, an amplification oligonucleotide for amplifying a target nucleic acid sequence contained in the target nucleic acid, and a capture probe for immobilizing the target nucleic acid on a solid support; b) after step a), forming a hybrid complex in the sample which comprises the capture probe, the target nucleic acid and the amplification oligonucleotide; c) immobilizing the hybrid complex on the solid support and removing components of the sample which are not part of the hybrid complex formed in step b); and d) exposing the target nucleic acid to amplification conditions, such that the amplification oligonucleotide is enzymatically extended to form a complementary copy of the target nucleic acid sequence. The organism may be chemically, mechanically, and/or thermally lysed, but is preferably lysed without the aid of mechanical means, such as sonication. To effect killing and lysis of the organism, the sample can be heated to a temperature of from about 60° C. to at least about 95° C. for at least about 15, 20 or 30 minutes. The detergent is preferably a cationic detergent, such as lithium lauryl sulfate, which is present at a final concentration of about 0.1 to about 5% (v/v). To facilitate hybridization in step b) without adversely affecting lysis of the organism in step a) of the method, the salt concentration is preferably about 0.6 M to about 0.9 M. This method is suitable for use with respiratory samples, including sputum samples, and may be used with other Gram positive bacilli, fungi and similarly difficult to lyse organisms.

Other features and advantages of the invention will be apparent from the following description of the preferred embodiments thereof and from the claims.

DESCRIPTION OF THE PREFERRED EMBODIMENTS

The present invention describes oligonucleotides targeted to nucleic acids derived from the 23S rRNA or rDNA of members of the TB complex which are particularly useful for determining the presence or amount of TB complex organisms in a test sample. The oligonucleotides can aid in detecting TB complex organisms in different ways, such as by functioning as detection probes, helper probes, capture probes and/or amplification oligonucleotides. Detection probes of the present invention can preferentially hybridize to a target sequence present in nucleic acid derived from the TB complex organisms under stringent hybridization conditions to form detectable duplexes which indicate the presence of one or more members of the TB complex in a test sample. Probes of the present invention are believed to be capable of distinguishing between TB complex organisms and their known closest phylogenetic neighbor. Helper probes of the present invention can hybridize to a target sequence present in nucleic acid derived from TB complex organisms under stringent hybridization conditions and can be used to enhance the formation of detection probe:target nucleic acid duplexes. Capture probes of the present invention can hybridize to a target sequence present in nucleic acid derived from a TB complex organism under assay conditions and can be used to separate target nucleic acid from other components of a clinical specimen. Amplification oligonucleotides of the present invention can hybridize to a target sequence present in nucleic acid derived from a TB complex organism under amplification conditions and can be used, for example, as primers in amplification reactions to generate multiple copies of TB complex-derived nucleic acid. The probes and amplification oligonucleotides can be used in assays for the detection and/or quantitation of members of the TB complex in a test sample.

A. Definitions

The following terms have the indicated meanings in the specification unless expressly indicated to have a different meaning.

By "sample" or "test sample" is meant any substance suspected of containing a target organism or nucleic acid derived from the target organism. The substance may be, for example, an unprocessed clinical specimen, such as a respiratory specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device. In the claims, the terms "sample" and "test sample" may refer to specimen in its raw form or to any stage of processing to release, isolate and purify nucleic acid derived from target organisms in the specimen. Thus, within a method of use claim, each reference to a "sample" or "test sample" may refer to a substance suspected of containing nucleic acid derived from the target organism or organisms at different stages of processing and is not limited to the initial form of the substance in the claim.

By "lyse" or "lysis" is meant, with reference to a cell, to cause or to be in an altered state permitting nucleic acid to be released therefrom. As used herein, the terms "lyse" and "lysis" do not require dissolution or destruction of a cell in order for the nucleic acid to be released.

By "target nucleic acid" or "target" is meant a nucleic acid containing a target nucleic acid sequence.

By "target nucleic acid sequence," "target sequence" or "target region" is meant a specific deoxyribonucleotide or ribonucleotide sequence comprising all or part of the nucleotide sequence of a single-stranded nucleic acid molecule.

By "oligonucleotide" or "oligomer" is meant a polymer made up of two or more nucleoside subunits or nucleobase subunits coupled together. The oligonucleotide may be DNA and/or RNA and analogs thereof. The sugar groups of the nucleoside subunits may be ribose, deoxyribose and analogs thereof, including, for example, ribonucleosides having a 2'-O-methylsubstitution to the ribofuranosyl moiety. (Oligonucleotides including nucleoside subunits having 2' substitutions and which are useful as detection probes, capture probes and/or amplification oligonucleotides are disclosed by Becker et al., "Method for Amplifying Target Nucleic Acids Using Modified Primers," U.S. Pat. No. 6,130,038.) The nucleoside subunits may be joined by linkages such as phosphodiester linkages, modified linkages, or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine. (DNA analogs having a pseudo-peptide backbone are commonly referred to as "peptide nucleic acids" or "PNA", and are disclosed by Nielsen et al., "Peptide Nucleic Acids," U.S. Pat. No. 5,539,082.) Other non-limiting examples of oligonucleotides or oligomers contemplated by the present invention include nucleic acid analogs containing bicyclic and tricyclic nucleoside and nucleotide analogs referred to as "Locked Nucleic Acids," "Locked Nucleoside Analogues" or "LNA." (Locked Nucleic Acids are disclosed by Wang, "Conformationally Locked Nucleosides and Oligonucleotides," U.S. Pat. No. 6,083,482; Imanishi et al., "Bicyclonucleoside and Oligonucleotide Analogues," U.S. Pat. No. 6,268,490; and Wengel et al., "Oligonucleotide Analogues," U.S. Pat. No. 6,670,461.) Any nucleic acid analog is contemplated by the present invention, provided that the modified oligonucleotide can hybridize to a target nucleic acid under stringent hybridization conditions or amplification conditions. In the case of detection probes, the modified oligonucleotides must also be capable of preferentially hybridizing to the target nucleic acid under stringent hybridization conditions.

Oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of an oligonucleotide is as a detection probe. Oligonucleotides may also be used as capture probes and amplification oligonucleotides.

By "detection probe" or "probe" is meant a structure comprising an oligonucleotide having a base sequence sufficiently complementary to its target nucleic acid sequence to form a probe:target hybrid stable for detection under stringent hybridization conditions. As would be understood by someone having ordinary skill in the art, the oligonucleotide is an isolated nucleic acid molecule, or an analog thereof, in a form not found in nature without human intervention (e.g., recombined with foreign nucleic acid, isolated, or purified to some extent). The probes of this invention may have additional nucleosides or nucleobases complementary to nucleotides outside of the targeted region so long as such nucleosides or nucleobases do not prevent hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promotor sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "substantially homologous," "substantially corresponding," or "substantially corresponds" is meant that the subject oligonucleotide has a base sequence containing an at least 10 contiguous base region that is at least 80% homologous, preferably at least 90% homologous, and most preferably 100% homologous to an at least 10 contiguous base region present in a reference base sequence (excluding RNA and DNA equivalents). (Those skilled in the art will readily appreciate modifications that could be made to the hybridization assay conditions at various percentages of homology to permit hybridization of the oligonucleotide to the target sequence while preventing unacceptable levels of non-specific hybridization.) The degree of similarity is determined by comparing the order of nucleobases making up the two sequences and does not take into consideration other structural differences that may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0 to 2 base differences.

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "hybridization" or "hybridize" is meant the ability of two completely or partially complementary nucleic acid strands to come together under specified hybridization assay conditions in a parallel or preferably antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., ROGER L. P. ADAMS ET AL., THE BIOCHEMISTRY OF THE NUCLEIC ACIDS (11$^{th}$ ed. 1992).)

By "preferentially hybridize" is meant that under stringent hybridization conditions, detection probes can hybridize to their target nucleic acids to form stable probe:target hybrids indicating the presence of at least one organism of interest, and there is not formed a sufficient number of stable probe: non-target hybrids to indicate the presence of non-targeted organisms, especially phylogenetically closely related organisms. Thus, the probe hybridizes to target nucleic acid to a sufficiently greater extent than to non-target nucleic acid to enable one having ordinary skill in the art to accurately detect the presence (or absence) of nucleic acid derived from TB complex organisms, as appropriate, and distinguish its presence from that of a phylogenetically closely related organism in a test sample. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. Preferential hybridization requires that there be at least a 10-fold difference between target and non-target hybridization signals in a test sample, although the difference is preferably at least a 100-fold difference, and more preferably at least a 1,000-fold difference. Most preferably, non-target hybridization signals in a test sample are no more than the background signal level.

By "stringent hybridization conditions," or "stringent conditions" is meant conditions permitting a detection probe to preferentially hybridize to a target nucleic acid (preferably rRNA or rDNA derived from TB complex organisms) and not to nucleic acid derived from a closely related non-target microorganism (e.g., M. celatum). Stringent hybridization conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. Preferred hybridization assay conditions for detecting target nucleic acids derived from TB complex organisms with the probes of the present invention correspond to a temperature of about 60° C. when the salt concentration is in the range of about 0.6-0.9 M. Specific hybridization assay conditions are set forth infra in the Examples section and in the section entitled "Detection Probes to Ribosomal Nucleic Acid of TB Complex Organisms." Other acceptable stringent hybridization conditions could be easily ascertained by those having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

By "consists essentially of" or "consisting essentially of," when used with reference to an oligonucleotide herein, is meant that the oligonucleotide has a base sequence substantially homologous to a specified base sequence and may have up to four additional bases and/or two bases deleted therefrom. Thus, these phrases contain both a sequence length limitation and a sequence variation limitation. Any additions or deletions are non-material variations of the specified base sequence which do not prevent the oligonucleotide from having its claimed property, such as being able to preferentially hybridize under stringent hybridization conditions to its target nucleic acid over non-target nucleic acids. The oligonucleotide may contain a base sequence substantially similar to a specified nucleic acid sequence without any additions or deletions. However, a probe or primer containing an oligonucleotide consisting essentially of (or which consists essentially of) a specified base sequence may include other nucleic acid molecules which do not participate in hybridization of the probe to the target nucleic acid and which do not affect such hybridization.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means that do not require a probe associated label. For instance, the detection method may include a probe-coated substrate that is optically active and sensitive to changes in mass at its surface. Mass changes result in different reflective and transmissive properties of the optically active substrate in response to light and serve to indicate the presence or amount of immobilized target nucleic acid. (This exemplary form of optical detection is disclosed by Nygren et al., "Devices and Methods for Optical Detection of Nucleic Acid Hybridization," U.S. Pat. No. 6,060,237.) Other means for detecting the formation of a nucleic acid duplex that do not require the use of a labeled probe include the use of binding agents, which include intercalating agents such as ethidium bromide. See, e.g., Higuchi, "Homogenous Methods for Nucleic Amplification and Detection," U.S. Pat. No. 5,994,056.

By "amplification oligonucleotide" or "primer" is meant an oligonucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification oligonucleotide is designed to initiate RNA synthesis, the primer may contain a base sequence which is non-complementary to the target sequence but which is recognized by a RNA polymerase such as a T7, T3, or SP6 RNA polymerase. An amplification oligonucleotide may contain a 3' terminus that is modified to prevent or lessen the rate or amount of primer extension. (See, e.g., McDonough et al., "Methods of Amplifying Nucleic Acids Using Promoter-Containing Primer Sequences," U.S. Pat. No. 5,766,849, disclose primers and promoter-primers having modified or blocked 3'-ends.) While the amplification oligonucleotides of the present invention may be chemically synthesized or derived from a vector, they are not naturally occurring nucleic acid molecules.

By "nucleic acid amplification" or "target amplification" is meant increasing the number of nucleic acid molecules having at least one target nucleic acid sequence. Target amplification according to the present invention may be either linear or exponential, although exponential amplification is preferred.

By "amplification conditions" is meant conditions permitting nucleic acid amplification. Acceptable amplification conditions could be readily ascertained without the exercise of anything more than routine experimentation by someone having ordinary skill in the art depending on the particular method of amplification employed.

By "antisense," "opposite sense," or "negative sense" is meant a nucleic acid molecule perfectly complementary to a reference, or sense, nucleic acid molecule.

By "sense," "same-sense," or "positive sense" is meant a nucleic acid molecule perfectly homologous to a reference nucleic acid molecule.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as the target nucleic acid.

By "derived" is meant that the referred to nucleic acid is obtained directly from an organism or is the product of a nucleic acid amplification. Thus, a nucleic acid that is "derived" from an organism may be, for example, an antisense RNA molecule which does not naturally exist in the organism.

By "capture probe" is meant an oligonucleotide that is capable of binding to a target nucleic acid (preferably in a region other than that targeted by a detection probe) and, either directly or indirectly, to a solid support, thereby providing means for immobilizing and isolating the target nucleic acid in a test sample. The capture probe includes a target binding region that hybridizes to the target nucleic acid. Although the capture probe may include a member of ligand-ligate binding pair (e.g., avidin-biotin linkage) for immobilizing the capture probe on a solid support, preferred capture probes include an immobilized probe binding region that hybridizes to an immobilized probe bound to a solid support. While the capture probe preferably hybridizes to both the target nucleic acid and the immobilized probe under stringent conditions, the target binding and the immobilized probe binding regions of the capture probe may be designed to bind to their target sequences under different hybridization conditions. In this way, the capture probe may be designed so that it first hybridizes to the target nucleic acid under more favorable in solution kinetics before adjusting the conditions to permit hybridization of the immobilized probe binding region to the immobilized probe. The target binding and immobilized probe binding regions may be contained within the same oligonucleotide, directly adjoining each other or separated by one or more optionally modified nucleotides, or these regions may be joined to each other by means of a non-nucleotide linker.

By "target binding region" is meant that portion of an oligonucleotide which stably binds to a target sequence present in a target nucleic acid, a DNA or RNA equivalent of the target sequence or a complement of the target sequence under assay conditions. The assay conditions may be stringent hybridization conditions or amplification conditions.

By "immobilized probe binding region" is meant that portion of an oligonucleotide which hybridizes to an immobilized probe under assay conditions.

By "homopolymer tail" in the claims is meant a contiguous base sequence of at least 10 identical bases (e.g., 10 contiguous adenines or thymines).

By "immobilized probe" is meant an oligonucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "isolate" or "isolating" is meant that at least a portion of the target nucleic acid present in a test sample is concentrated within a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "purify" or "purifying" is meant that one or more components of the test sample are removed from one or more other components of the sample. Sample components to be purified may include viruses, nucleic acids or, in particular, target nucleic acids in a generally aqueous solution phase which may also include undesirable materials such as proteins, carbohydrates, lipids, non-target nucleic acid and/or labeled probes. Preferably, the purifying step removes at least about 70%, more preferably at least about 90% and, even more preferably, at least about 95% of the undesirable components present in the sample.

By "phylogenetically closely related" is meant that the organisms are closely related to each other in an evolutionary sense and therefore would be expected to have a higher total nucleic acid sequence homology than organisms that are more distantly related. Organisms occupying adjacent and next to adjacent positions on the phylogenetic tree are closely related. Organisms occupying positions farther away than adjacent or next to adjacent positions on the phylogenetic tree will still be closely related if they have significant total nucleic acid sequence homology.

B. Hybridization Conditions and Probe Design

Hybridization reaction conditions, most importantly the temperature of hybridization and the concentration of salt in the hybridization solution, can be selected to allow the detection probes or, in some cases, amplification oligonucleotides of the present invention to preferentially hybridize to a TB complex-derived target nucleic acid and not to other non-target nucleic acids suspected of being present in a test sample. At decreased salt concentrations and/or increased temperatures (conditions of increased stringency) the extent of nucleic acid hybridization decreases as hydrogen bonding between paired nucleobases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular detection probe or amplification oligonucleotide and those of the target and non-target nucleic acids on the other, one or more mismatches will not necessarily defeat the ability of an oligonucleotide contained in the probe or amplification oligonucleotide to hybridize to the target nucleic acid and not to non-target nucleic acids.

The detection probes of the present invention were chosen, selected, and/or designed to maximize the difference between the melting temperatures of the probe:target hybrid ($T_m$, defined as the temperature at which half of the potentially double-stranded molecules in a given reaction mixture are in a single-stranded, denatured state) and the $T_m$ of a mismatched hybrid formed between the probe and ribosomal RNA (rRNA) or ribosomal DNA (rDNA) of the phylogenetically most closely-related organisms expected to be present in the test sample, but not sought to be detected. While the unlabeled amplification oligonucleotides and capture probes need not have such an extremely high degree of specificity as the detection probe to be useful in the present invention, they are designed in a similar manner to preferentially hybridize to one or more target nucleic acids over other nucleic acids under specified amplification, assay or stringent hybridization conditions.

Within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the detection probes described herein were identified by noting variations in the homology of the aligned sequences.

The sequence evolution at each of the variable regions is mostly divergent. Because of the divergence, corresponding rRNA variable regions of more distant phylogenetic relatives of the TB complex organisms show greater differences from the rRNA of the TB complex organisms than do the rRNAs of phylogenetically closer relatives. Sufficient variation between the TB complex organisms and other organisms was observed to identify preferred target sites and to design detection probes useful for distinguishing the TB complex organisms over non-TB complex organisms in a test sample, particularly *M. celatum*, the most closely related organism to the TB complex organisms.

Merely identifying putatively unique potential target nucleotide sequences does not guarantee that a functionally species-specific detection probe may be made to hybridize to TB complex rRNA or rDNA comprising that sequence. Various other factors will determine the suitability of a nucleic acid locus as a target site for genus-specific or species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art and are disclosed by Hogan et al., "Nucleic Acid Probes for Detection and/or Quantitation of Non-Viral Organisms," U.S. Pat. No. 5,840,488; Hogan et al., "Nucleic Acid Probes to *Mycobacterium gordonae,*" U.S. Pat. No. 5,216,143; and Kohne, "Method for Detection, Identification and Quantitation of Non-Viral Organisms," U.S. Pat. No. 4,851,330. The contents of each of the foregoing references is hereby incorporated by reference herein.

The desired temperature of hybridization and the hybridization solution composition (such as salt concentration, detergents, and other solutes) can also greatly affect the stability of double-stranded hybrids. Conditions such as ionic strength and the temperature at which a probe will be allowed to hybridize to a target must be taken into account in constructing a genus-specific or species-specific probe. The thermal stability of hybrid nucleic acids generally increases with the ionic strength of the reaction mixture. On the other hand, chemical reagents that disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize to their targets under conditions of high stringency. Under such conditions only single nucleic acid strands having a high degree of complementarity will hybridize to each other. Single nucleic acid strands without such a high degree of complementarity will not form hybrids. Accordingly, the stringency of the assay conditions determines the amount of complementarity that should exist between two nucleic acid strands in order to form a hybrid. Stringency is chosen to maximize the difference in stability between the hybrid formed between the probe and the target nucleic acid and potential hybrids between the probe and any non-target nucleic acids present in a test sample.

Proper specificity may be achieved by minimizing the length of the detection probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe non-target hybrids. In designing probes, the differences in these $T_m$ values should be as large as possible (preferably 2-5° C. or more). Manipulation of the $T_m$ can be accomplished by changes to probe length and probe composition (e.g., GC content versus AT content).

In general, the optimal hybridization temperature for oligonucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are known in the art. (See, e.g., J. Sambrook et al., Molecular Cloning: A Laboratory Manual, ch. 11 ($2^{nd}$ ed. 1989).)

A preferred method to determine $T_m$ measures hybridization using the well known Hybridization Protection Assay (HPA) disclosed by Arnold et al., "Homogenous Protection Assay," U.S. Pat. No. 5,283,174, the contents of which are hereby incorporated by reference herein. The $T_m$ can be measured using HPA in the following manner. Probe molecules are labeled with an acridinium ester and permitted to form probe:target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2-5° C. increments. This solution is then diluted with a mild alkaline borate buffer (600 mM boric acid, 240 mM NaOH, 1% (v/v) TRITON® X-100 detergent, pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® HC+ Luminometer (Gen-Probe Incorporated; San Diego, Calif.; Cat. No. 4747). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see, e.g., Hogan et al., U.S. Pat. No. 5,840,488).

To ensure specificity of a detection probe for its target, it is preferable to design probes that hybridize only to target nucleic acid under conditions of high stringency. Only highly complementary sequences will form hybrids under conditions of high stringency. Accordingly, the stringency of the assay conditions determines the amount of complementarity needed between two sequences in order for a stable hybrid to form. Stringency should be chosen to maximize the difference in stability between the probe:target hybrid and potential probe:non-target hybrids.

Examples of specific stringent hybridization conditions are provided in the Examples section infra. Of course, alternative stringent hybridization conditions can be determined by those of ordinary skill in the art based on the present disclosure. (See, e.g., SAMBROOK ET AL., supra, ch. 11.)

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another that differs from it merely by a single base. While it is possible for nucleic acids that are not perfectly complementary to hybridize, the longest stretch of perfectly complementary bases, as well as the base compositions, will generally determine hybrid stability.

Regions of rRNA known to form strong internal structures inhibitory to hybridization are less preferred target regions. Likewise, probes with extensive self-complementarity are generally to be avoided, with specific exceptions being discussed below. If a strand is wholly or partially involved in an intramolecular or intermolecular hybrid, it will be less able to participate in the formation of a new intermolecular probe:target hybrid without a change in the reaction conditions. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

A genomic ribosomal nucleic acid (rDNA) target occurs naturally in a double-stranded form, as does the product of the polymerase chain reaction (PCR). These double-stranded targets are naturally inhibitory to hybridization with a probe and require denaturation prior to hybridization. Appropriate denaturation and hybridization conditions are known in the art (see, e.g., Southern, E. M., *J. Mol. Biol.*, 98:503 (1975)).

A number of formulae are available which will provide an estimate of the melting temperature for perfectly matched oligonucleotides to their target nucleic acids. One such formula is the following: $T_m = 81.5 + 16.6(\log_{10}[Na+]) + 0.41$ (fraction G+C)−(600/N) (where N=the length of the oligonucleotide in number of nucleotides) provides a good estimate of the $T_m$ for oligonucleotides between 14 and 60 to 70 nucleotides in length. From such calculations, subsequent empirical verification or "fine tuning" of the $T_m$ may be made using screening techniques well known in the art. For further information on hybridization and oligonucleotide probes reference may be made to SAMBROOK ET AL., supra, ch. 11. This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Preferably, the amplification oligonucleotides of the present invention are oligodeoxynucleotides and are sufficiently long to be used as a substrate for the synthesis of extension products by a nucleic acid polymerase. Optimal amplification oligonucleotide length should take into account several factors, including the temperature of reaction, the structure and base composition of the amplification oligonucleotide, and how the amplification oligonucleotide is to be used. For example, for optimal specificity the oligonucleotide amplification oligonucleotide generally should be at least 12 bases in length, depending on the complexity of the target nucleic acid sequence. If such specificity is not essential, shorter amplification oligonucleotides may be used. In such a case, it may be desirable to carry out the reaction at cooler temperatures in order to form stable hybrid complexes with the template nucleic acid.

Useful guidelines for designing amplification oligonucleotides and detection probes with desired characteristics are described infra in the section entitled "Preparation of Oligonueleotides." Optimal sites for amplifying and probing contain at least two, and preferably three, conserved regions of TB complex nucleic acid. These regions are about 15 to 350 bases in length, and preferably between about 15 and 150 bases in length.

The degree of amplification observed with a set of amplification oligonucleotides (e.g., primers and/or promoter-primers) depends on several factors, including the ability of the amplification oligonucleotides to hybridize to their specific target sequences and their ability to be extended or copied enzymatically. While amplification oligonucleotides of different lengths and base compositions may be used, amplification oligonucleotides preferred in this invention have target binding regions of 15 to 40 bases with a predicted $T_m$ to target of about 42° C.

Parameters affecting probe hybridization, such as $T_m$, complementarity, and secondary structure of the target sequence, also affect amplification oligonucleotide hybridization and therefore performance of the amplification oligonucleotides. The degree of non-specific extension (primer-dimer or non-target copying) can also affect amplification efficiency. Thus, amplification oligonucleotides are selected to have low self-complementarity or cross-complementarity, particularly at the 3' ends of their sequences. Notwithstanding, it should be noted that the "signal primers" described infra could be modified to include regions of self-complementarity, thereby transforming them into "molecular torch" or "molecular beacon" signal primers, such as these terms are defined below. Lengthy homopolymer runs and high GC content are avoided to reduce spurious primer extension. Computer programs are available to aid in this aspect of the design, including Oligo Tech analysis software which is available from Oligos Etc. Inc. and can be accessed on the World Wide Web at www.oligosetc.com/analysis.php using a hypertext transfer protocol (http) in the URL.

A nucleic acid polymerase used in conjunction with the amplification oligonucleotides of the present invention refers to a chemical, physical, or biological agent that incorporates either ribonucleotides or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the typical anti-parallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilis* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly synthesized template strand may be made available for hybridization with a second primer or promoter-primer by other means, such as through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification oligonucleotide, or both, may be a promoter-primer. In some applications, the amplification oligonucleotides may only consist of promoter-primers which are complementary to the sense strand, as disclosed by Kacian et al., "Nucleic Acid Sequence Amplification Method, Composition and Kit," U.S. Pat. No. 5,554,516, the contents of which are hereby incorporated by reference herein, and by Becker et al., U.S. Patent Publication No. US-2006-0046265-A1. A promoter-primer usually contains an oligonucleotide that is not complementary to a nucleotide sequence present in the target nucleic acid molecule or primer extension product(s) (see Kacian et al., "Nucleic Acid Sequence Amplification Methods," U.S. Pat. No. 5,399,491, the contents of which are hereby incorporated by reference herein). These non-complementary sequences may be located 5' to the complementary sequences on the amplification oligonucleotide and may provide a locus for initiation of RNA synthesis when made double-stranded through the action of a nucleic acid polymerase. The promoter thus provided may allow for the in vitro transcription of multiple. RNA copies of the target nucleic acid sequence. It will be appreciated that when reference is made to a primer in this specification, such reference is intended to include the primer aspect of a promoter-primer as well, unless the context of the reference clearly indicates otherwise.

In some amplification systems (see, e.g., Dattagupta et al., "Isothermal Strand Displacement Nucleic Acid Amplification," U.S. Pat. No. RE39,007, the contents of which are hereby incorporated by reference herein), the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' ends to prevent enzymatic digestion. Alternatively, the nucleic acid polymerase may be modified to remove the 5' exonuclease activity, such as by treatment with a protease that generates an active polymerase fragment with no such nuclease activity. In such a case the primers need not be modified at their 5' ends.

1. Preparation of Oligonucleotides

The detection probes, capture probes and amplification oligonucleotides of the present invention can be readily prepared by methods known in the art. Preferably, the oligonucleotides are synthesized using solid phase methods. For example, Caruthers describes using standard phosphoramidite solid-phase chemistry to join nucleotides by phosphodiester linkages. See Caruthers et al., "Chemical Synthesis of Deoxynucleotides by the Phosphoramidite Method," *Methods Enzymol.*, 154:287 (1987). Automated solid-phase chemical synthesis using cyanoethyl phosphoramidite precursors has been described by Barone. See Barone et al., "In Situ Activation of bis-dialkylaminephosphines—a New Method for Synthesizing Deoxyoligonucleotides on Polymer Supports," *Nucleic Acids Res.*, 12(10):4051 (1984). Likewise, Bhatt, "Method and Reagent for Sulfurization of Organophosphorous Compounds," U.S. Pat. No. 5,449,769, discloses a procedure for synthesizing oligonucleotides containing phosphorothioate linkages. In addition, Riley et al., "Process for the Purification of Oligomers," U.S. Pat. No. 5,811,538, disclose the synthesis of oligonucleotides having different linkages, including methylphosphonate linkages. Moreover, methods for the organic synthesis of oligonucleotides are known to those of skill in the art and are described in, for example, SAMBROOK ET AL., supra, ch. 10. Each of the foregoing references is hereby incorporated by reference herein.

Following synthesis of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present invention, whether detection probes, capture probes or amplification oligonucleotides, may be modified with chemical groups to enhance their performance or to facilitate the characterization of amplification products.

For example, backbone-modified oligonucleotides such as those having phosphorothioate, methylphosphonate, 2'-O-alkyl, or peptide groups which render the oligonucleotides resistant to the nucleolytic activity of certain polymerases or to nuclease enzymes may allow the use of such enzymes in an amplification or other reaction. Another example of a modification involves using non-nucleotide linkers incorporated between nucleotides in the nucleic acid chain of a probe or primer, and which do not prevent hybridization of a probe or hybridization and elongation of a primer. (See Arnold et al., "Non-Nucleotide Linking Reagents for Nucleotide Probes," U.S. Pat. No. 6,031,091, the contents of which are hereby incorporated by reference herein.) The oligonucleotides of the present invention may also contain mixtures of the desired modified and natural nucleotides.

The 3' end of an amplification oligonucleotide, particularly a promoter-primer, may be modified or blocked to prevent or inhibit initiation of DNA synthesis, as disclosed by Kacian et al., U.S. Pat. No. 5,554,516, and Becker et al., U.S. Patent Publication No. US-2006-0046265-A1. The 3' end of the primer can be modified in a variety of ways well known in the art. By way of example, appropriate modifications to a promoter-primer can include the addition of ribonucleotides, 3' deoxynucleotide residues (e.g., cordycepin), 2',3'-dideoxynucleotide residues, modified nucleotides such as phosphorothioates, and non-nucleotide linkages such as those disclosed by Arnold et al. in U.S. Pat. No. 6,031,091 or alkanediol modifications (see Wilk et al., "Backbone-Modified Oligonucleotides Containing a Butanediol-1,3 Moiety as a 'Vicarious Segment' for the Deoxyribosyl Moiety—Synthesis and Enzyme Studies," *Nucleic Acids Res.*, 18(8):2065 (1990), the contents of which are hereby incorporated by reference herein), or the modification may simply consist of a region 3' to the priming sequence that is non-complementary to the target nucleic acid sequence. Additionally, a mixture of different 3' blocked promoter-primers or of 3' blocked and unblocked promoter-primers may increase the efficiency of nucleic acid amplification, as described therein.

As disclosed above, the 5' end of primers may be modified to be resistant to the 5'-exonuclease activity present in some nucleic acid polymerases. Such modifications can be carried out by adding a non-nucleotide group to the terminal 5' nucleotide of the primer using techniques such as those disclosed by Arnold et al., U.S. Pat. No. 6,031,091.

Once synthesized, a selected oligonucleotide may be labeled by any well known method (see, e.g., SAMBROOK ET AL., supra, ch. 10). Useful labels include radioisotopes as well as non-radioactive reporting groups. Isotopic labels include $^3$H, $^{35}$S, $^{32}$P, $^{125}$I, $^{57}$Co, and $^{14}$C. Isotopic labels can be introduced into the oligonucleotide by techniques known in the art such as nick translation, end labeling, second strand synthesis, the use of reverse transcription, and by chemical methods. When using radiolabeled probes, hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as disclosed by Arnold et al., U.S. Pat. No. 6,031,091. Non-isotopic labels include fluorescent molecules (individual labels or combinations of labels, such as the fluorescence resonance energy transfer (FRET) pairs disclosed by Tyagi et al., "Detectably Labeled Dual Conformation Oligonucleotide Probes," U.S. Pat. No. 5,925,517), chemiluminescent molecules, enzymes, cofactors, enzyme substrates, haptens, or other ligands.

With the detection probes of the present invention, the probes are preferably labeled using of a non-nucleotide linker with an acridinium ester. Acridinium ester labeling may be performed as disclosed by Arnold et al., "Acridinium Ester Labelling and Purification of Nucleotide Probes," U.S. Pat. No. 5,185,439, the contents of which are hereby incorporated by reference herein.

2. Amplification of TB Complex Ribosomal Nucleic Acid

The amplification oligonucleotides of the present invention are directed to 23S regions of ribosomal nucleic acid derived from the TB complex organisms. These amplification oligonucleotides may flank, overlap, or be contained within at least one of the target sequences of a detection probe (or its complement) used to detect the presence of TB complex organisms in a nucleic acid amplification assay. As indicated above, the amplification oligonucleotides may also include non-complementary bases at their 5' ends comprising a promoter sequence able to bind a RNA polymerase and direct RNA transcription using the target nucleic acid as a template. A T7 promoter sequence, such as SEQ ID NO:29, may be used.

Amplification oligonucleotides of the present invention are capable of amplifying a target region of a target nucleic acid derived from the 23S rRNA or rDNA of the TB complex organisms under amplification conditions. In one embodiment, a first amplification oligonucleotide is provided that preferably comprises a target binding region up to 40 bases in length which stably hybridizes, under amplification conditions, to a target sequence contained with the target nucleic acid or its complement. The target binding region of the first amplification oligonucleotide has a base sequence that comprises, overlaps with, consists essentially of, substantially corresponds to, consists of, or is contained within and includes at least 12 of 15 contiguous bases of the base sequence of SEQ ID NO:21, SEQ ID NO:22, SEQ ID NO:23 or SEQ ID NO:24.

In another embodiment, a second amplification oligonucleotide is provided that preferably comprises a target binding region up to 40 bases in length which stably hybridizes, under amplification conditions, to a target sequence contained within the target nucleic acid or its complement. The target binding region of the second amplification oligonucleotide has a base sequence that comprises, overlaps with, consists essentially of, substantially corresponds to, consists of, or is contained within and includes at least 12 of 15 contiguous bases of the base sequence of SEQ ID NO:25, SEQ ID NO:26, SEQ ID NO:27 or SEQ ID NO:28.

The amplification oligonucleotides of the present invention are preferably provided in sets of at least two amplification oligonucleotides for amplifying TB complex-derived nucleic acid. Each set of amplification oligonucleotides preferably has at least one antisense amplification oligonucleotide and at least one sense amplification oligonucleotide. Preferred sets of amplification oligonucleotides comprise at least one of the above-described first amplification oligonucleotides in combination with at least one of the above-described second amplification oligonucleotides. More preferably, the set of amplification oligonucleotides is used in a transcription-based amplification procedure and at least one of the amplification oligonucleotides includes a promoter sequence recognized by an RNA polymerase.

Amplification oligonucleotides of the present invention may have modifications, such as blocked 3' and/or 5' termini (as discussed above) or sequence additions including, but not limited to, a specific nucleotide sequence recognized by a RNA polymerase (e.g., a promoter sequence for T7, T3 or SP6 RNA polymerase), a sequence which enhances initiation or elongation of RNA transcription by a RNA polymerase, or a sequence which may provide for intra-molecular base pairing and encourage the formation of secondary or tertiary nucleic acid structures.

Amplification oligonucleotides are used in any suitable nucleic acid amplification procedure now known or later developed. Existing amplification procedures include the polymerase chain reaction (PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., *Nucleic Acids Res.*, 20:1691-1696 (1992); Fahy et al., "Self-sustained Sequence Replication (3SR): An Isothermal Transcription-Based Amplification System Alternative to PCR," *PCR Methods and Applications*, 1:25-33 (1991); Kacian et al., U.S. Pat. No. 5,399,491; Kacian et al., "Nucleic Acid Sequence Amplification Methods," U.S. Pat. No. 5,480,784; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," European Patent Application No. 1 020 534 A1; Dattagupta et al., "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997). (Each of the foregoing amplification references is hereby incorporated by reference herein.) Any other amplification procedure which meets the definition of "nucleic acid amplification" supra is also contemplated by the inventors.

Amplification oligonucleotides of the present invention are preferably unlabeled but may include one or more reporter groups to facilitate detection of a target nucleic acid in combination with or exclusive of a detection probe. A wide variety of methods are available to detect an amplified target sequence. For example, the nucleotide substrates or the amplification oligonucleotides can include a detectable label that is incorporated into newly synthesized DNA. The resulting labeled amplification product is then generally separated from the unused labeled nucleotides or amplification oligonucleotides and the label is detected in the separated product fraction. (See, e.g., Wu, "Detection of Amplified Nucleic Acid Using Secondary Capture Oligonucleotides and Test Kit," U.S. Pat. No. 5,387,510.)

A separation step is not required, however, if the amplification oligonucleotide is modified by, for example, linking it to an interacting label pair, such as two dyes which form a donor/acceptor dye pair. The modified amplification oligonucleotide can be designed so that the fluorescence of one dye pair member remains quenched by the other dye pair member, so long as the amplification oligonucleotide does not hybridize to target nucleic acid, thereby physically separating the two dyes. Moreover, the amplification oligonucleotide can be further modified to include a restriction endonuclease recognition site positioned between the two dyes so that when a hybrid is formed between the modified amplification oligonucleotide and target nucleic acid, the restriction endonuclease recognition site is rendered double-stranded and available for cleavage or nicking by an appropriate restriction endonuclease. Cleavage or nicking of the hybrid then separates the two dyes, resulting in a change in fluorescence due to decreased quenching which can be detected as an indication of the presence of the target organism in the test sample. This type of modified amplification oligonucleotide, referred to as a "signal primer," is disclosed by Nadeau et al., "Detection of Nucleic Acids by Fluorescence Quenching," U.S. Pat. No. 6,054,279, the contents of which are hereby incorporated by reference herein.

Substances which can serve as useful detectable labels are well known in the art and include radioactive isotopes, fluorescent molecules, chemiluminescent molecules, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled oligonucleotide probe and measuring the resulting hybrids in any conventional manner. In particular, the product can be assayed by hybridizing a chemiluminescent acridinium ester-labeled oligonucleotide probe to the target sequence, selectively hydrolyzing the acridinium ester present on unhybridized probe, and measuring the chemiluminescence produced from the remaining acridinium ester in a luminometer. (See, e.g., Arnold et al., U.S. Pat. No. 5,283,174, and NORMAN C. NELSON ET AL., NONISOTOPIC PROBING, BLOTTING, AND SEQUENCING, ch. 17 (Larry J. Kricka ed., 2d ed. 1995).)

D. Sample Processing

Sample processing prior to amplification or detection of a target sequence may be necessary or useful for discriminating a target sequence from non-target nucleic acid present in a sample. Respiratory samples (e.g., sputum, bronchoalveolar lavage and pleural fluid samples) are initially processed in accordance with known procedures, such as a NALC-NaOH or NaOH digestion. See, e.g., GABY E. PFYFFER ET AL., MANUAL OF CLINICAL MICROBIOLOGY, ch. 36 (Patrick R. Murray et al. eds., 8$^{th}$ ed. 2003), the contents of which are hereby incorporated by reference herein. *Mycobacterium tuberculosis* can be found in other sources as well, including lung tissue, lymph nodes, blood and cerebral spinal fluid.

Sample processing procedures may include, for example, direct or indirect immobilization of nucleic acids and/or oligonucleotides from the liquid phase in a heterogeneous assay. With some procedures, such immobilization may require multiple hybridization events. Ranki et al., "Detection of Microbial Nucleic Acids by a One-Step Sandwich Hybridization Test," U.S. Pat. Nos. 4,486,539 and 4,563,419, for example, disclose a one-step nucleic acid "sandwich" hybridization method involving the use of a solid-phase bound nucleic acid having a target complementary sequence and a labeled nucleic acid probe which is complementary to a distinct region of the target nucleic acid. Stabinsky, "Methods and Kits for Performing Nucleic Acid Hybridization Assays," U.S. Pat. No. 4,751,177, discloses methods including a "mediator" polynucleotide that reportedly overcomes sensitivity problems associated with Ranki's method resulting from leakage of immobilized probe from the solid support. Instead of directly immobilizing the target nucleic acid, the mediator polynucleotides of Stabinsky are used to bind and indirectly immobilize target polynucleotide:probe polynucleotide complexes which have formed free in solution.

Any known solid support may be used for sample processing, such as matrices and particles free in solution. The solid support may be, for example, nitrocellulose, nylon, glass, polyacrylate, mixed polymers, polystyrene, silane polypropylene and, preferably, particles having a magnetic charge to facilitate recovering sample and/or removing unbound nucleic acids or other sample components. Particularly preferred supports are magnetic spheres that are monodisperse (i.e., uniform in size ±5%), thereby providing consistent results, which is particularly advantageous for use in an automated procedure. See, e.g., Ammann et al., "Automated Process for Isolating and Amplifying a Target Nucleic Acid Sequence," U.S. Pat. No. 6,335,166, the contents of which are hereby incorporated by reference herein.

An oligonucleotide for immobilizing a target nucleic acid on a solid support may be joined directly or indirectly to the solid support by any linkage or interaction which is stable under assay conditions (e.g., conditions for amplification and/or detection). Referred to herein as an "immobilized probe," this oligonucleotide may bind directly to the target nucleic acid or it may include a base sequence region, such as a homopolymeric tract (e.g., a poly dT) or a simple short repeating sequence (e.g., an AT repeat), which hybridizes to a complementary base sequence region present on a capture probe. Direct joining occurs when the immobilized probe is joined to the solid support in the absence of an intermediate group. For example, direct joining may be via a covalent linkage, chelation or ionic interaction. Indirect joining occurs when the immobilized probe is joined to the solid support by one or more linkers. A "linker" is a means for binding at least two different molecules into a stable complex and contains one or more components of a binding partner set.

Members of a binding partner set are able to recognize and bind to each other. Binding partner sets may be, for example, receptor and ligand, enzyme and substrate, enzyme and cofactor, enzyme and coenzyme, antibody and antigen, sugar and lectin, biotin and streptavidin, ligand and chelating agent, nickel and histidine, substantially complementary oligonucleotides, and complementary homopolymeric nucleic acids or homopolymeric portions of polymeric nucleic acids. Components of a binding partner set are the regions of the members that participate in binding.

A preferred sample processing system having practical advantages in terms of its ease of use and rapidity comprises an immobilized probe containing a base sequence which is complementary to a base sequence of a capture probe, referred to herein as an "immobilized probe binding region." The capture probe additionally contains a base sequence, referred to herein as a "target binding region," which may specifically hybridize to a target sequence contained in a target nucleic acid under assay conditions. (While specificity of the target binding region of the capture probe for a region of the target nucleic acid is desirable to minimize the number of non-target nucleic acids remaining from the sample after a separation step, it is not a requirement of the capture probes of the present invention if the capture probes are being used solely to isolate target nucleic acid.) If the capture probe is not being employed to isolate a target nucleic acid for subsequent amplification of a target sequence, the capture probe may further include a detectable label attached within or near the target binding region, such as a substituted or unsubstituted acridinium ester. The labeled capture probe may be used in a homogeneous or semi-homogenous assay to specifically detect hybrid nucleic acids without detecting single-stranded nucleic acids, such as the capture probe. A preferred homogenous assay which could be used with this system is the hybridization protection assay (HPA), which is discussed above in the section entitled "Hybridization Conditions and Probe Design." Following the HPA format, label associated with capture probes which have not hybridized to target nucleic acids would be hydrolyzed with the addition of a mild base, while label associated with capture probe:target hybrids would be protected from hydrolysis.

An advantage of this latter assay system is that only a single target-specific hybridization event (capture probe:target) is necessary for target detection, rather than multiple such events (e.g., capture probe:target and probe:target or probe:amplicon) which are required in other sample processing procedures described herein. Also, fewer oligonucleotides in an assay tend to make the assay faster and simpler to optimize, since the overall rate at which a target nucleic acid is captured and detected is limited by the slowest hybridizing oligonucleotide. While the target binding region of a capture probe may be less specific in alternative assay systems, it must still be rare enough to avoid significant saturation of the capture probe with non-target nucleic acids. Thus, the requirement that two separate and specific target sequences be identified in these alternative systems could place constraints on the identification of an appropriate target. By contrast, only one such target sequence is needed when the capture probe simultaneously functions as the detection probe.

Whichever approach is adopted, the assay needs to include means for detecting the presence of the target nucleic acid in the test sample. A variety of means for detecting target nucleic acids are well known to those skilled in the art of nucleic acid detection, including means which do not require the presence of a detectable label. Nevertheless, probes including a detectable label are preferred. A labeled probe for detecting the presence of a target nucleic acid would have to include a base sequence which is substantially complementary and specifically hybridizes to a target sequence contained in the target nucleic acid. Once the probe stably binds to the target nucleic acid, and the resulting target:probe hybrid has been directly or indirectly immobilized, unbound probe can be washed away or inactivated and the remaining bound probe can be detected and/or measured. Preferred sample processing systems combine the elements of detection and nucleic acid amplification. These systems first directly or indirectly immobilize a target nucleic acid using a capture probe, the captured target nucleic acid is purified by removing inter alia cellular debris, non-target nucleic acid and amplification inhibitors from the sample-containing vessel, which is followed by amplification of a target sequence contained in the target nucleic acid. Amplified product is then detected, preferably in solution with a labeled probe. (The target nucleic acid may remain in the immobilized state during amplification or it may be eluted from the solid support prior to amplification using appropriate conditions, such as by first incubating at a temperature above the $T_m$ of the capture probe:target complex and/or the $T_m$ of the capture probe:immobilized probe complex.) A preferred embodiment of this system is disclosed by Weisburg et al., "Two-Step Hybridization and Capture of a Polynucleotide," U.S. Pat. No. 6,110,678, the contents of which are hereby incorporated by reference herein. In this system, the capture probe hybridizes to the target nucleic acid and an immobilized probe hybridizes to the capture probe:target complex under different hybridization conditions. Under a first set of hybridization conditions, hybridization of the capture probe to the target nucleic acid is favored over hybridization of the capture probe to the immobilized probe. Thus, under this first set of conditions, the capture probe is in solution rather than bound to a solid support, thereby maximizing the concentration of the free capture probe and utilizing favorable liquid phase kinetics for hybridization to the target nucleic acid. After the capture probe has had sufficient time to hybridize to the target nucleic acid, a second set of hybridization conditions is imposed permitting in the capture probe:target complex to hybridize to the immobilized probe, thereby isolating the target nucleic acid in the sample solution. The immobilized target nucleic acid may then be purified, and a target sequence present in the target nucleic acid may be amplified and detected. A purification procedure which includes one or more wash steps is generally desirable when working with crude samples (e.g., clinical samples) to prevent enzyme inhibition and/or nucleic acid degradation due to substances present in the sample.

A preferred amplification method is the transcription-mediated amplification method disclosed by Kacian et al., "Nucleic Acid Sequence Amplification Methods," U.S. Pat. No. 5,480,789, the contents of which are hereby incorporated by reference herein. In accord with this method, a promoter-primer having a 3' region complementary to a portion of the target and a 5' promoter region and a primer having the same nucleotide sequence as a portion of the target are contacted with a target RNA molecule. The primer and promoter-primer define the boundaries of the target region to be amplified, including both the sense present on the target molecule and its complement, and thus the length and sequence of the amplicon. In this preferred embodiment, the amplification oligonucleotides and immobilized target RNA are contacted in the presence of effective amounts of Moloney murine leukemia virus-derived reverse transcriptase and T7 RNA polymerase, both ribonucleotide and deoxyribonucleotide triphosphates, and necessary salts and cofactors at 42° C. Under these conditions, nucleic acid amplification occurs, resulting predominantly in the production of RNA amplicons of a sense opposite to that of the target nucleic acid. These amplicons can then be detected in solution by, for example, using an acridinium ester-labeled hybridization assay probe of the same sense as the target nucleic acid, employing HPA, as disclosed by Arnold et al. in U.S. Pat. No. 5,283,174.

The 3' terminus of the immobilized probe and the capture probe are preferably "capped" or blocked to prevent or inhibit their use as templates for nucleic acid polymerase activity. Capping may involve adding 3' deoxyribonucleotides (such as cordycepin), 3',2'-dideoxynucleotide residues, non-nucleotide linkers, such as those disclosed by Arnold et al. in U.S. Pat. No. 6,031,091, alkane-diol modifications, or non-complementary nucleotide residues at the 3' terminus.

Those skilled in the art will recognize that the above-described methodology is amenable, either as described or with obvious modifications, to various other amplification schemes, including, for example, the polymerase chain reaction (PCR), Qβ replicase-mediated amplification, self-sustained sequence replication (3SR), strand displacement amplification (SDA), nucleic acid sequence-based amplification (NASBA), loop-mediated isothermal amplification (LAMP), and the ligase chain reaction (LCR).

E. Capture Probes for Isolating Ribosomal Nucleic Acid of TB Complex Organisms

Capture probes of the present invention are designed to bind to and isolate nucleic acid derived from the 23S rRNA or rDNA of the TB complex organisms. As such, the capture probes preferably include both a target binding region and an immobilized probe binding region. The target binding region of the capture probes includes a base sequence which hybridizes to a target sequence contained in TB complex-derived nucleic acid under assay conditions. While not essential, the target binding region preferably exhibits specificity for the target sequence in the presence of non-target nucleic acid under assay conditions. The immobilized probe binding region has a base sequence which hybridizes to an immobilized probe comprising a polynucleotide, or a chimeric containing polynucleotide sequences, which is joined to a solid support present in the test sample, either directly or indirectly. The target binding region and the immobilized probe binding region may be joined to each other directly or by means of, for example, a nucleotide base sequence, an abasic sequence or a non-nucleotide linker.

In a preferred embodiment, capture probes according to the present invention are up to 100 bases in length and include a target binding region that stably binds to TB complex-derived nucleic acid under assay conditions and which comprises, overlaps with, consists essentially of, substantially corresponds to, consists of, or is contained within and includes at least 12 of 15 contiguous bases of a base sequence selected from the group consisting of SEQ ID NO:13, SEQ ID NO:14, SEQ ID NO:15, SEQ ID NO:16, SEQ ID NO:17, SEQ ID NO:18, SEQ ID NO:19 and SEQ ID NO:20. The immobilized probe binding region of these preferred capture probes comprises a base sequence which hybridizes to an immobilized probe joined directly or indirectly to a solid support provided to the test sample under assay conditions. Preferably, the immobilized probe binding region comprises a homopolymeric region (e.g., poly dA) located at the 3' end of the capture probe which is complementary to a homopolymeric region (e.g., poly dT) located at the 5' end of the immobilized probe. The immobilized probe binding region preferably consists of the base sequence of SEQ ID NO:30 tttaaaaaaaaaaaaaaaaaa-aaaaaaaaaaaaa. (The tail portion includes a 5'-ttt-3' spacer sequence interposed between the target binding portion and the oligo(dA)$_{30}$ sequence to make the capture probe more flexible for binding to the immobilized probe binding region.) Other base sequences may be incorporated into the immobilized probe binding region, including, for example, short repeating sequences.

To prevent undesirable cross-hybridization reactions, the capture probes of the present invention preferably exclude nucleotide base sequences, other than the nucleotide base sequence of the target binding region, which can stably bind to nucleic acid derived from any organism which may be present in the test sample under assay conditions. Consistent with this approach, and in order to maximize the immobilization of capture probe:target complexes which are formed, the nucleotide base sequence of the immobilized probe binding region is preferably designed so that it can stably bind to a nucleotide base sequence present in the immobilized probe under assay conditions and not to nucleic acid derived from any organism which may be present in the test sample.

The target binding region and the immobilized probe binding region of the capture probe may be selected so that the capture probe:target complex has a higher $T_m$ than the $T_m$ of the capture probe:immobilized probe complex. In this way, a first set of conditions may be imposed which favors hybridization of the capture probe to the target sequence over the immobilized probe, thereby providing for optimal liquid phase hybridization kinetics for hybridization of the capture probe to the target sequence. Once sufficient time has passed for the capture probe to bind to the target sequence, a second set of less stringent conditions may be imposed which allows for hybridization of the capture probe to the immobilized probe.

Capture probes of the present invention may also include a label or a pair of interacting labels for direct detection of the target sequence in a test sample. Non-limiting examples of labels, combinations of labels and means for labeling probes are set forth supra in the section entitled "Preparation of Oligonucleotides" and infra in the section entitled "Detection Probes to Ribosomal Nucleic Acid of TB Complex Organisms." A particularly useful method for detecting the presence of a capture probe hybridized to a target nucleic acid is the Hybridization Protection Assay (HPA), which is described above in the section entitled "Hybridization Conditions and Probe Design." HPA is a homogenous assay which distinguishes between probe hybridized to target nucleic acid and probe which remains unhybridized. Signal detected from an HPA reaction vessel provides an indication of the presence or amount of target organisms in the test sample.

Despite their application in a direct detection assay, the most common use of capture probes is in the isolation and purification of target nucleic acid prior to amplifying a target sequence contained in the target nucleic acid. By isolating and purifying the target nucleic acid prior to amplification, the number of unintended amplification reactions (i.e., amplification of non-target nucleic acid) can be severely limited. And, to prevent or inhibit the capture probe itself from functioning as a template for nucleic acid polymerase activity in the presence of amplification reagents and under amplification conditions, the 3' end of the capture probe may be capped or blocked. Examples of capping agents include 3' deoxyribonucleotides, 3',2'-dideoxynucleotide residues, non-nucleotide linkers, alkane-diol modifications, and non-complementary nucleotide residues at the 3' terminus.

In a preferred embodiment, a sample suspected of containing TB complex organisms is exposed to a detergent-containing lytic composition at a temperature and for a period of time sufficient to kill the TB complex organisms and to release target nucleic acid therefrom. (It is believed that this method could be use with other difficult to lyse organisms, including other Gram positive bacilli and fungi.) Because TB complex organisms are highly infectious agents transmitted by contaminated aerosols, it is important to kill TB complex organisms during sample processing. To kill TB complex organisms, sample exposed to the lytic composition is heated to a temperature of about 60° C. for at least about one hour to at least about 95° C. for at least about 15 minutes, preferably for at least about 20 minutes, and more preferably for at least about 30 minutes. Skilled molecular biologists will be able to readily adjust the temperature and time parameters to effect killing and lysis of TB complex and other organisms based on the guidance provided herein.

The detergent is provided in an amount sufficient to lyse mycobacteria and is preferably a cationic detergent at a final reaction concentration of about 0.1 to about 5% (v/v), more preferably about 0.1 to about 3% (v/v), even more preferably about 0.1 to about 1.5% (v/v), and most preferably about 0.1 to about 0.3% (v/v). Because it was found that lysis is most effective under low total ionic strength, it is desirable to keep the monovalents contributed by the detergent to a minimum when combined with the other monovalents of the lytic composition. The detergent also more effectively inactivates released nucleases at the indicated concentrations. Examples of suitable cationic detergents include lithium lauryl sulfate (LLS) and sodium dodecyl sulfate (SDS), although LLS is preferred because it is more soluble than SDS at higher concentrations.

In addition to the detergent, the lytic composition further includes a capture probe and an amplification oligonucleotide, both of which complex with the released target nucleic under a second set of conditions, which includes a temperature that is lower than the melting temperatures of hybrids formed between the target nucleic acid and the capture probe and amplification oligonucleotide. The salt concentration of the mixture containing the lytic composition and the sample is preferably in the range of about 0.6 M to about 0.9 M, a range which was found to facilitate hybridization of the capture probe and amplification oligonucleotide to the target nucleic acid without substantially interfering with killing and lysis of TB complex organisms. The amplification oligonucleotide may be any primer capable of binding to the target nucleic acid and being enzymatically extended in the presence of a nucleic acid polymerase under the second set of conditions, including a promoter-primer useful in a transcription-based amplification reaction. In a preferred embodiment, the lytic composition further comprises an internal control and an associated amplification oligonucleotide, each of which complexes with a capture probe under the second set of conditions.

Following the formation of a complex comprising the capture probe, target nucleic acid and amplification oligonucleotide, the complex is immobilized on a solid support and isolated in a reaction container while amplification inhibitors present in the sample are removed from the complex. Examples of capture probes and solid supports that can be used in this method include those described supra; however, solid supports comprised of magnetically charged particles or beads are preferred because they limit the time and manipulation steps required to purify the target nucleic acid. The magnetically charged particles or beads can be localized with magnets strategically positioned adjacent or with in a reaction container, without centrifugation, during a standard wash procedure. Since detergents present in many wash buffers constitute amplification inhibitors, it may be preferable to follow the wash steps with one or more rinses using a buffer containing no or a low concentration of an inhibiting detergent. After the wash procedure, the target nucleic acid may be exposed to reagents and conditions permitting amplification of a target sequence contained in the target nucleic acid. Such reagents will include the polymerases, nucleoside triphosphates and cofactors needed to effect a particular amplification reaction, examples of which are described herein. The conditions of the amplification may include a temperature that is lower than the temperature needed to form the captureprobe:target nucleic acid:amplification complex following the killing and lysis step.

The foregoing method for obtaining and amplifying targeted nucleic acid from TB complex organisms is suitable for use with a variety of sample types, including respiratory samples (e.g., sputum), cerebral spinal fluid, gastric aspirates and pleural fluids. If a sputum sample is used, it is preferably a sediment prepared following a digestion-decontamination procedure using N-acetyl-L-cysteine as a mucolytic agent, sodium hydroxide as a decontaminating agent for lysing non-mycobacterial organisms present in the sample, and sodium citrate to prevent inactivation of the acetylcysteine. See PATRICIA T, KENT ET AL., PUBLIC HEALTH MYCOBACTERIOLOGY A GUIDE FOR THE LEVEL III LABORATORY, pp. 36-39 (U.S. Department of Health and Human Services 1985), the contents of which are hereby incorporated by reference herein. Advantageously, the method permits the simultaneous killing and lysing of these potentially pathogenic organisms (e.g., *Mycobacterium tuberculosis*). Further, mechanical means, such as vortexing, sonication, French press and glass bead milling, are not required to lyse organisms in this method. Mechanical lysing means are disfavored because of the increased risk of disseminating a contaminating aerosol, either in the form of nucleic acid carryover contamination or viable organisms. And, because an amplification oligonucleotide needed to initiate amplification is present in the lytic composition, the reaction time is much faster than if the amplification oligonucleotide was separately added.

F. Detection Probes to Ribosomal Nucleic Acid of TB Complex Organisms

This embodiment of the invention relates to novel detection probes. Hybridization is the association of two single strands of complementary nucleic acid to form a hydrogen-bonded double strand. A nucleic acid sequence able to hybridize to a nucleic acid sequence sought to be detected ("target sequence") can serve as a probe for the target sequence. Hybridization may occur between complementary nucleic acid strands, including DNA/DNA, DNA/RNA, and RNA/RNA, as well as between single-stranded nucleic acids wherein one or both strands of the resulting hybrid contain at least one modified nucleotide, nucleoside, nucleobase, and/or base-to-base linkage. In any case, two single strands of sufficient complementarity may hybridize to form a double-stranded structure in which the two strands are held together by hydrogen bonds between pairs of complementary bases. As described above, in general A is hydrogen-bonded to T or U, while G is hydrogen-bonded to C. At any point along the hybridized strands, therefore, the classical base pairs AT or AU, TA or UA, GC, or CG may be found. Thus, when a first single strand of nucleic acid contains sufficient contiguous complementary bases to a second, and those two strands are brought together under conditions that promote their hybridization, double-stranded nucleic acid will result. Accordingly, under appropriate conditions, double-stranded nucleic acid hybrids may be formed.

The rate and extent of hybridization is influenced by a number of factors. For instance, it is implicit that if one of the two strands is wholly or partially involved in a hybrid, it will be less able to participate in the formation of a new hybrid. By designing a probe so that a substantial portion of the sequence of interest is single-stranded, the rate and extent of hybridization may be greatly increased. Also, if the target is an integrated genomic sequence it will naturally occur in a double-stranded form, as is the case with a product of PCR. These double-stranded targets are naturally inhibitory to hybridization with a single-stranded probe and require denaturation (in at least the region to be targeted by the probe) prior to the hybridization step. In addition, there can be intra-molecular and inter-molecular hybrids formed within a probe if there is sufficient self-complementarity. Regions of the nucleic acid known or expected to form strong internal structures inhibitory to hybridization are less preferred. Examples of such structures include hairpin loops. Likewise, probes with extensive self-complementarity generally should be avoided. All these undesirable structures can be avoided through careful probe design, and commercial computer programs are available to search for these types of interactions, such as the Oligo Tech analysis software.

In some applications, however, probes exhibiting at least some degree of self-complementarity are desirable to facilitate detection of probe:target duplexes in a test sample without first requiring the removal of unhybridized probe prior to detection. "Molecular torches" are a type of self-complementary probe that is disclosed by Becker et al., "Molecular Torches," U.S. Pat. No. 6,361,945, the contents of which are hereby incorporated by reference herein. Molecular torches have distinct regions of self-complementarity, referred to as "the target binding domain" and "the target closing domain," which are connected by a joining region and which hybridize to one another under predetermined hybridization assay conditions. When exposed to denaturing conditions, the complementary regions (which may be fully or partially complementary) of a molecular torch melt, leaving the target binding domain available for hybridization to a target sequence when the predetermined hybridization assay conditions are restored. And when exposed to strand displacement conditions, a portion of the target sequence binds to the target binding domain and displaces the target closing domain from the target binding domain. Molecular torches are designed so that the target binding domain favors hybridization to the target sequence over the target closing domain. The target binding domain and the target closing domain of a molecular torch include interacting labels (e.g., luminescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label or labels associated therewith.

Another example of detection probes having self-complementarity are the molecular beacons disclosed by Tyagi et al. in U.S. Pat. No. 5,925,517. Molecular beacons include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and quencher, such as DABCYL and EDANS.

The rate at which a probe hybridizes to its target is one measure of the thermal stability of the target secondary structure in the probe region. The standard measurement of hybridization rate is the $C_ot_{1/2}$, which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. The $C_ot_{1/2}$ is found graphically by standard procedures. The probe:target hybrid melting temperature may be determined by isotopic methods well-known to those skilled in the art. The melting temperature ($T_m$) for a given hybrid will vary depending on the hybridization solution being used.

Preferred detection probes are sufficiently complementary to the target nucleic acid sequence, or its complement, to hybridize therewith under stringent hybridization conditions corresponding to a temperature of about 60° C. when the salt concentration is in the range of about 0.6-0.9 M. Preferred salts include lithium chloride, but other salts such as sodium chloride and sodium citrate also can be used in the hybridization solution. Examples of high stringency hybridization conditions are alternatively provided by 0.48 M sodium phosphate buffer, 0.1% sodium dodecyl sulfate, and 1 mM each of EDTA and EGTA at a temperature of about 60° C., or by 0.6 M LiCl, 1% lithium lauryl sulfate (LLS), 60 mM lithium succinate and 10 mM each of EDTA and EGTA at a temperature of about 60° C.

Thus, in a first aspect, the present invention features detection probes able to distinguish TB complex-derived nucleic acid from non-TB complex nucleic acid (e.g., *M. celatum*) by virtue of the ability of the detection probes to preferentially hybridize to TB complex-derived nucleic acid under stringent hybridization conditions. Specifically, the detection probes include an optionally modified oligonucleotide having a base sequence that is substantially complementary to a target sequence present in TB complex-derived nucleic acid.

In the case of a hybridization assay, the length of the target nucleic acid sequence and, accordingly, the length of the probe sequence can be important. In some cases, there may be several sequences from a particular region, varying in location and length, which will yield probes with the desired hybridization characteristics. In other cases, one sequence may have better hybridization characteristics than another that differs merely by a single base. While it is possible for nucleic acids that are not perfectly complementary to hybridize, the longest stretch of perfectly homologous base sequence will normally primarily determine hybrid stability. While probes of different lengths and base composition may be used, the probes preferred in the present invention are up to 100 bases in length, more preferably from 12 to 35 bases in length, and most preferably from 15 to 25 bases in length.

The detection probes include a base sequence that is substantially complementary to a target sequence present in 23S rRNA or rDNA of any of the TB complex organisms. Thus, the detection probes are able to stably hybridize to a target sequence derived from any of the TB complex organisms under stringent hybridization conditions. The detection probes may also have additional bases outside of the targeted nucleic acid region which may or may not be complementary to TB complex-derived nucleic acid but which are not complementary to nucleic acid derived from a non-target organism which may be present in the test sample.

The probes of the present invention may be designed to include a capture tail comprised of a base sequence (distinct from the base sequence intended to hybridize to the target sequence) that can hybridize under predetermined hybridization conditions to a substantially complementary base sequence present in an immobilized oligonucleotide that is joined to a solid support. The immobilized oligonucleotide is preferably joined to a magnetically charged particle that can be isolated in a reaction vessel during a purification step after a sufficient period of time has passed for the probe to hybridize to the target nucleic acid. (An example of an instrument which can be used to perform such a purification step is the DTS® 400 Target Capture System (Gen-Probe; Cat. No. 5105).) The probe is preferably designed so that the melting temperature of the probe:target hybrid is greater than the melting temperature of the probe:immobilized oligonucleotide hybrid. In this way, different sets of hybridization assay conditions can be employed to facilitate hybridization of the probe to the target nucleic acid prior to hybridization of the probe to the immobilized oligonucleotide, thereby maximizing the concentration of free probe and providing favorable liquid phase hybridization kinetics. This "two-step" target capture method is disclosed by Weisburg et al. in U.S. Pat. No. 6,110,678. Other target capture schemes which could be readily adapted to the present invention are well known in the art and include, for example, those disclosed by Ranki et al., U.S. Pat. No. 4,486,539; Stabinsky, U.S. Pat. No. 4,751,177; and Boom et al., "Process for Isolating Nucleic Acid," U.S. Pat. No. 5,234,809, each of which references is hereby incorporated by reference herein.

For TB complex detection probes, the terms "target nucleic acid sequence," "target nucleotide sequence," "target sequence," and "target region" all refer to a nucleic acid sequence present in the 23S rRNA or rDNA of the TB complex organisms, or a sequence complementary thereto, which is not identically present in the nucleic acid of a closely related species. Nucleic acids having nucleotide sequences complementary to a target sequence may be generated by target amplification techniques disclosed elsewhere herein.

The organism most closely related to the TB complex organisms is M. celatum. The detection probes of the present invention preferably distinguish nucleic acid derived from the TB complex organisms over nucleic acid derived from other mycobacterial organisms, but especially M. celatum. Additionally, the TB complex detection probes of the present invention can be used to distinguish TB complex-derived nucleic acid from any non-TB complex nucleic acid that does not stably hybridize with the probe(s) under stringent hybridization conditions.

In one embodiment, TB complex detection probes of the present invention are preferably up to 100 bases in length and have a target binding region that comprises, overlaps with, consists essentially of, substantially corresponds to, consists of, or is contained within and includes at least 12 of 15 contiguous bases of the base sequence of SEQ ID NO:1, SEQ ID NO:2, SEQ ID NO:3 or SEQ ID NO:4. In a preferred mode, a detection probe in accordance with the present invention includes an acridinium ester label joined to the probe in accordance with the teachings of Arnold et al. in U.S. Pat. Nos. 5,185,439 and 6,031,091. The probes preferentially hybridize under stringent hybridization conditions to a target nucleic acid derived from TB complex organisms over nucleic acid derived from non-TB complex organisms present in the test sample. In particular, the probes do not form hybrids stable for detection with nucleic acid derived from M. celatum under the conditions used.

Once synthesized, the probes may be labeled with a detectable label or reporter group by any well-known method. (See, e.g., SAMBROOK ET AL., supra, ch. 10.) The probe may be labeled with a detectable moiety such as a radioisotope, antigen or chemiluminescent moiety to facilitate detection of the target sequence. Useful labels include radioisotopes as well as non-radioactive reporting groups. Isotopic labels include $^{3}$H, $^{35}$S, $^{32}$P, $^{125}$I, $^{57}$Co and $^{14}$C. Isotopic labels can be introduced into an oligonucleotide by techniques known in the art such as nick translation, end labeling, second strand synthesis, reverse transcription and by chemical methods. When using radiolabeled probes, hybridization can be detected by techniques such as autoradiography, scintillation counting or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through use of non-nucleotide linker groups disclosed by Arnold et al. in U.S. Pat. No. 6,031,091. Non-isotopic labels include fluorescent molecules, chemiluminescent molecules, fluorescent chemiluminescent molecules, phosphorescent molecules, electrochemiluminescent molecules, chromophores, enzymes, enzyme cofactors, enzyme substrates, dyes and haptens or other ligands. Another useful labeling technique is a base sequence that is unable to stably hybridize to the target nucleic acid under stringent conditions. Probes of the present invention are preferably labeled with an acridinium ester. (Acridinium ester labeling is disclosed by Arnold et al. in U.S. Pat. No. 5,185,439.)

The selected detection probe can then be brought into contact with a test sample suspected of containing one or more TB complex organisms. Generally, the test sample is from a source that also contains unknown organisms. Typically, the source of the test sample will be a patient specimen, such as a sputum, bronchoalveolar lavage or pleural fluid sample. After bringing the probe into contact with nucleic acids derived from the test sample, the probe and sample-derived nucleic acids can be incubated under conditions permitting preferential hybridization of the probe to a target nucleic acid derived from TB complex organisms that may be present in the test sample in the presence of nucleic acid derived from other organisms present in the test sample.

Detection probes may also be combined with one or more unlabeled helper probes to facilitate binding to target nucleic acid derived from TB complex organisms. After a detection probe has hybridized to target nucleic acid present in the test sample, the resulting hybrid may be separated and detected by various techniques well known in the art, such as hydroxyapatite adsorption and radioactive monitoring. Other techniques include those which involve selectively degrading label associated with unhybridized probe and then measuring the amount of remaining label associated with hybridized probe, as disclosed by Arnold et al. in U.S. Pat. No. 5,283,174. The inventors particularly prefer this latter technique.

G. Helper Probes Used in the Detection of TB Complex Organisms

Another embodiment of this invention relates to helper probes. As mentioned above, helper probes can be used to facilitate hybridization of detection probes to their intended target nucleic acids, so that the detection probes more readily form probe:target nucleic acid duplexes than they would in the absence of helper probes. (See Hogan et al., "Means and Method for Enhancing Nucleic Acid Hybridization," U.S. Pat. No. 5,030,557, the contents of which are hereby incorporated by reference herein.) Each helper probe contains an oligonucleotide that is sufficiently complementary to a target nucleic acid sequence to form a helper probe:target nucleic acid duplex under stringent hybridization conditions. The stringent hybridization conditions employed with a given helper probe are determined by the conditions used for preferentially hybridizing the associated detection probe to the target nucleic acid.

Regions of single-stranded RNA and DNA can be involved in secondary and tertiary structures even under stringent hybridization conditions. Such structures can sterically inhibit or block hybridization of a detection probe to a target nucleic acid. Hybridization of the helper probe to the target nucleic acid alters the secondary and tertiary structure of the target nucleic acid, thereby rendering the target region more accessible by the detection probe. As a result, helper probes enhance the kinetics and/or the melting temperature of the detection probe:target nucleic acid duplex. Helper probes are generally selected to hybridize to nucleic acid sequences located near the target region of the detection probe.

Helper probes which can be used with the TB complex detection probes of the present invention are targeted to nucleic acid sequences within TB complex-derived nucleic acid. Likewise, helper probes which can be used with the TB complex detection probes of the present invention are targeted to nucleic acid sequences within TB complex-derived nucleic acid. Each helper probe comprises an optionally modified oligonucleotide which targets and stably hybridizes to a base region present in nucleic acid derived from any of the TB complex organisms under stringent hybridization conditions. Helper probes and their associated detection probes have different target sequences contained within the same target nucleic acid. The helper probes of the present invention are preferably oligonucleotides up to 100 bases in length, more preferably from 12 to 50 bases in length, and even more preferably from 18 to 40 bases in length.

Preferred TB complex helper probes useful in the present invention have a base sequence comprising, overlapping with, consisting essentially of, consisting of, substantially corresponding to, or contained within and includes at least 12 of 15 contiguous bases of the base sequence of SEQ ID NO:5, SEQ ID NO:6, SEQ ID NO:7, SEQ ID NO:8, SEQ ID NO:9, SEQ ID NO:10, SEQ ID NO:11 or SEQ ID NO:12. The helper probes are preferably employed in sets of two, where the first helper probe has a base sequence comprising, overlapping with, consisting essentially of, consisting of, substantially corresponding to, or contained within and includes at least 12 of 15 contiguous bases of the base sequence of SEQ ID NO:5, SEQ ID NO:6, SEQ ID NO:7 or SEQ ID NO:8, and where the second helper probe has a base sequence comprising, overlapping with, consisting essentially of, consisting of, substantially corresponding to, or contained within and includes at least 12 of 15 contiguous bases of the base sequence of SEQ ID NO:9, SEQ ID NO:10, SEQ ID NO:11 or SEQ ID NO:12. The preferred TB complex detection probe for use with the one or more helper probes has a target binding region comprising, overlapping with, consisting essentially of, consisting of, substantially corresponding to, or contained within and includes at least 12 of 15 contiguous bases of the base sequence of SEQ ID NO:1, SEQ ID NO:2, SEQ ID NO:3 or SEQ ID NO:4, where the detection probe preferentially hybridizes under stringent hybridization conditions to a TB complex-derived target nucleic acid over nucleic acid derived from non-TB complex organisms present in a test sample. In particular, the probe does not form a hybrid stable for detection with *M. celatum* nucleic acid under the conditions used.

H. Assay Methods

The present invention contemplates various methods for assaying for the presence or amount of nucleic acid derived from TB complex organisms in a test sample. One skilled in the art will understand that the exact assay conditions, probes, and/or amplification oligonucleotides used will vary depending on the particular assay format used and the source of the sample.

One aspect of the present invention relates to a method for determining the presence or amount of TB complex organisms in a test sample by contacting the test sample, under stringent hybridization conditions, with a detection probe capable of preferentially hybridizing under stringent hybridization conditions to a TB complex-derived target nucleic acid over nucleic acids from non-TB complex organisms present in the test sample. In such methods, detection probes of the present invention are preferably up to 100 bases in length and have a target binding region that comprises, overlaps with, consists essentially of, substantially corresponds to, consists of, or is contained within and includes at least 12 of 15 contiguous bases of the base sequence of SEQ ID NO:1, SEQ ID NO:2, SEQ ID NO:3 or SEQ ID NO:4. The detection probes may further include labels to facilitate detection in the test sample. In a preferred mode, the detection probes of this method include acridinium ester labels joined to the probes in accordance with the teachings of Arnold et al. in U.S. Pat. Nos. 5,185,439 and 6,031,091.

In one preferred embodiment, the method for determining the presence or amount of TB complex organisms in a test sample may also include the step of contacting the test sample with one or more helper probes for facilitating hybridization of the probe to the target nucleic acid. While the helper probes may be added to the sample before or after the addition of the detection probe, the helper probes and detection probe are preferably provided to the test sample at the same time. The base sequence of a preferred helper probe for use in this method comprises, overlaps with, consists essentially of, consists of, substantially corresponds to, or is contained within and includes at least 12 of 15 contiguous bases of the base sequence of SEQ ID NO:5, SEQ ID NO:6, SEQ ID NO:7, SEQ ID NO:8, SEQ ID NO:9, SEQ ID NO:10, SEQ ID NO:11 or SEQ ID NO:12. A pair of helper probes is preferably provided to the test sample in this method, with the first helper probe having a base sequence comprising, overlapping with, consisting essentially of, consisting of, substantially corresponding to, or contained within and includes at least 12 of 15 contiguous bases of the base sequence of SEQ ID NO:5, SEQ ID NO:6, SEQ ID NO:7 or SEQ ID NO:8, and with the second helper probe having a base sequence comprising, overlapping with, consisting essentially of, consisting of, substantially corresponding to, or contained within and includes at least 12 of 15 contiguous bases of the base sequence of SEQ ID NO:9, SEQ ID NO:10, SEQ ID NO:11 or SEQ ID NO:12. The helper probes of this method are preferably used in combination with a detection probe, where the base sequence of the detection probe comprises, overlaps with, consists essentially of, consists of, substantially corresponds to, or is contained within and includes at least 12 of 15 contiguous bases of the base sequence of SEQ ID NO:1, SEQ ID NO:2, SEQ ID NO:3 or SEQ ID NO:4, and where the detection probe preferentially hybridizes to TB complex-derived nucleic acid over nucleic acid derived from non-TB complex organisms present in the test sample under stringent hybridization conditions.

Another aspect of the present invention relates to a method for amplifying TB complex-derived nucleic acid in a test sample by contacting the test sample under amplification conditions with one or more amplification oligonucleotides which, when contacted with a nucleic acid polymerase, will bind to or cause elongation through a nucleic acid region having a base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28. The amplification oligonucleotides optionally include a nucleic acid sequence recognized by a RNA polymerase or which enhances initiation or elongation by a RNA polymerase. Combinations of amplification oligonucleotides that can be used in this method are set forth above under the heading "Amplification of TB Complex Ribosomal Nucleic Acid."

In preferred embodiments, the methods for amplifying TB complex-derived nucleic acid in a test sample further include the step of contacting the test sample under stringent hybridization conditions with a detection probe capable of preferentially hybridizing under stringent hybridization conditions to an amplified TB complex target nucleic acid over nucleic acids from non-TB complex organisms present in the test sample. While the test sample is generally contacted with the detection probe after a sufficient period for amplification has passed, the amplification oligonucleotides and detection probe may be added to the sample in any order, as when the detection probe is a self-hybridizing probe, such as a molecular torch discussed supra. This step of contacting the test sample with a detection probe is performed so that the presence or amount of TB complex organisms in a test sample can be determined. Preferred detection probes for use in this method are described in the section entitled "Detection Probes to Ribosomal Nucleic Acid of TB Complex Organisms" supra.

Still another aspect of the present invention relates to a method for immobilizing a target nucleic acid derived from a TB complex organism in a test sample which comprises providing to the test sample a capture probe having a target binding region and an immobilized probe binding region under a first set of hybridization conditions permitting the capture probe to stably bind the target nucleic acid, thereby forming a capture probe:target complex, and a second set of hybridization conditions permitting the capture probe to stably bind to an immobilized probe in the test sample, thereby forming an immobilized probe:capture probe:target complex. The first and second sets of hybridization conditions may be the same or different and the capture probe:target complex remains stable under the second set of hybridization conditions. The target binding region of this capture probe comprises, consists essentially of, overlaps with, substantially corresponds to, consists of, or is contained within and includes at least 12 of 15 contiguous bases of the base sequence of SEQ ID NO:13, SEQ ID NO:14, SEQ ID NO:15, SEQ ID NO:16, SEQ ID NO:17, SEQ ID NO:18, SEQ ID NO:19 or SEQ ID NO:20. A purifying step preferably follows the immobilizing step to remove one or more components of the test sample that might interfere with or prevent amplification or specific detection of a target sequence contained in the immobilized target nucleic acid. This method for immobilizing and optionally purifying a TB complex-derived nucleic may precede any of the methods described above for amplifying and/or detecting the presence of a target nucleic acid derived from a TB complex organism. If a purifying step is included, the target nucleic acid may be indirectly eluted from the immobilized probe or directly eluted from the capture probe of the immobilized probe:capture probe:target complex by altering the sample conditions prior to amplifying or detecting the target sequence.

I. Diagnostic Systems

The present invention also contemplates diagnostic systems in kit form. A diagnostic system of the present invention may include a kit that contains, in an amount sufficient for at least one assay, any of the detection probes, capture probes and/or amplification oligonucleotides of the present invention in a packaging material. Typically, the kits will also include instructions recorded in a tangible form (e.g., contained on paper or an electronic medium, such as a disk, CD-ROM, DVD or video tape) for using the packaged probes and/or amplification oligonucleotides in an amplification and/or detection assay for determining the presence or amount of TB complex organisms in a test sample.

The various components of the diagnostic systems may be provided in a variety of forms. For example, the required enzymes, the nucleotide triphosphates, the probes and/or primers may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present invention may contain a reconstitution reagent for reconstituting the lyophilized reagents of the kit. In preferred kits for amplifying target nucleic acid derived from a TB complex organism, the enzymes, nucleotide triphosphates and required cofactors for the enzymes are provided as a single lyophilized reagent that, when reconstituted, forms a proper reagent for use in the present amplification methods. In these kits, a lyophilized primer reagent may also be provided. In other preferred kits, lyophilized probe reagents are provided.

Typical packaging materials would include solid matrices such as glass, plastic, paper, foil, micro-particles and the like, capable of holding within fixed limits detection probes and/or amplification oligonucleotides of the present invention. Thus, for example, the packaging materials can include glass vials used to contain sub-milligram (e.g., picogram or nanogram) quantities of a contemplated probe or primer, or they can be microtiter plate wells to which probes or primers of the present invention have been operatively affixed, i.e., linked so as to be capable of participating in an amplification and/or detection method of the present invention.

The instructions will typically indicate the reagents and/or concentrations of reagents and at least one assay method parameter that might be, for example, the relative amounts of reagents to use per amount of sample. In addition, such specifics as maintenance, time periods, temperature and buffer conditions may also be included.

The diagnostic systems of the present invention contemplate kits having any of the detection probes, helper probes, capture probes and/or amplification oligonucleotides described herein, whether provided individually or in one of the preferred combinations described above, for use in amplifying and/or determining the presence or amount of TB complex organisms in a test sample.

J. Examples

Examples are provided below illustrating different aspects and embodiments of the invention. It is believed that these examples accurately reflect the details of experiments actually performed, however, it is possible that some minor discrepancies may exist between the work actually performed and the experimental details set forth below which do not affect the conclusions of these experiments. Skilled artisans will appreciate that these examples are not intended to limit the invention to the specific embodiments described therein.

1. Organism Lysis

Whole cells in the examples below were chemically and thermally lysed in a detergent-containing buffer described in the "Reagents" section infra. In addition to facilitating cell lyses, the buffer protects released RNAs by inhibiting the activity of RNAses present in test samples. The buffer also contained amplification primers and capture probes for use in the isolation, purification and amplification of target nucleic acid sequences.

2. Oligonucleotide Synthesis

Oligonucleotides featured in the examples below include detection probes, helper probes, amplification oligonucleotides and capture probes. These oligonucleotides were synthesized using standard phosphoramidite chemistry, various methods of which are well known in the art. See, e.g., Caruthers et al., *Methods in Enzymol.*, 154:287 (1987). Synthesis was performed using an Expedite™ 8909 Nucleic Acid Synthesizer (Applied Biosystems; Foster City, Calif.). The detection probes were also synthesized to include a non-nucleotide linker, as disclosed by Arnold et al. in U.S. Pat. Nos. 5,585,481 and 5,639,604, and labeled with a chemiluminescent acridinium ester, as disclosed by Arnold et al. in U.S. Pat. No. 5,185,439.

3. Transcription-Mediated Amplification

Amplification of a target sequence in the following examples was by a Transcription-Mediated Amplification (TMA) procedure disclosed by, for example, Kacian et al. in U.S. Pat. Nos. 5,399,491 and 5,480,784 and by LEE ET AL., supra, ch. 8. TMA is an isothermal amplification procedure which allows for a greater than one billion-fold increase in copy number of the target sequence using reverse transcriptase and RNA polymerase (see "Enzyme Reagent" below). A TMA reaction involves converting a single-stranded target sequence to a double-stranded DNA intermediate by reverse transcriptase in the presence of a pair of amplification oligonucleotides, one of which has a 5' RNA polymerase-specific promoter sequence. In this embodiment, the DNA intermediate includes a double-stranded promoter sequence which is recognized by a RNA polymerase and directs transcription of the target sequence into hundreds of copies of RNA. Each of these transcribed RNA molecules, in turn, can be converted to a double-stranded DNA intermediate which is used for producing additional RNA. Thus, the TMA reaction proceeds exponentially. The particulars of the TMA reactions used in the following examples are set forth below.

4. Reagents

Various reagents are identified in the examples below, which include a specimen dilution buffer, a target capture reagent, an amplification reagent, a primer reagent, an enzyme reagent, a probe reagent, a selection reagent, and detection reagents. The formulations and pH values (where relevant) of these reagents were as follows.

Specimen Dilution Buffer. The "Specimen Dilution Buffer" contained 300 mM HEPES, 3% (w/v) lithium lauryl sulfate, 44 mM LiCl, 120 mM LiOH, 40 mM EDTA, 20 nM TB complex capture probe, 60 nM TB complex T7 promoter-primer, 17.6 nM IC capture probe, 32 nM IC T7 promoter-primer, 0.1 Fg/FL 1 micron magnetic particles Sera-Mag™ MG-CM Carboxylate Modified (Seradyn, Inc.; Indianapolis, Ind.; Cat. No. 24152105-050450) having oligo(dT)$_{14}$ covalently bound thereto, adjusted to pH 7.4 with 2 M LiOH.

Wash Solution. The "Wash Solution" contained 10 mM HEPES, 6.5 mM NaOH, 1 mM EDTA, 0.3% (v/v) ethyl alcohol, 0.02% (w/v) methyl paraben, 0.01% (w/v) propyl paraben, 150 mM NaCl, and 0.1% (w/v) sodium lauryl sulfate, adjusted to pH 7.5 with 4 M NaOH.

Amplification Reagent. The "Amplification Reagent" was a lyophilized form of a 3.5 mL solution containing 26.7 mM rATP, 5.0 mM rCTP, 33.3 mM rGTP and 5.0 mM rUTP, 125 mM HEPES, 8% (w/v) trehalose, 1.33 mM dATP, 1.33 mM dCTP, 1.33 mM dGTP and 1.33 mM dTTP, adjusted to pH 7.7 with 4 M NaOH.

Amplification Reagent Reconstitution Solution. The Amplification Reagent was reconstituted to a full volume of 9.5 mL with an "Amplification Reagent Reconstitution Solution" containing 0.4% (v/v) ethyl alcohol, 0.10% (w/v) methyl paraben, 0.02% (w/v) propyl paraben, 33 mM KCl, 30.6 mM MgCl$_2$, 0.003% phenol red.

Enzyme Reagent. The "Enzyme Reagent" was a lyophilized form of a 1.35 mL solution containing 20 mM HEPES, 125 mM N-acetyl-L-cysteine, 0.1 mM EDTA, 0.2% (v/v) TRITON7 X-100 detergent, 0.2 M trehalose, 900 RTU/FL Moloney murine leukemia virus ("MMLV") reverse transcriptase, and 200 U/FL T7 RNA polymerase, adjusted to pH 7.0 with 4 M NaOH. (One reverse transcriptase unit ("RTU") of activity for MMLV reverse transcriptase is defined as the incorporation of 1 nmol dTMP into DE81 filter-bound product in 20 minutes at 37° C. using (poly(rA)-p(dT)$_{12-18}$) as the substrate, and for T7 RNA polymerase, one unit ("U") of activity is defined as the production of 5.0 fmol RNA transcript in 20 minutes at 37° C.)

Enzyme Reagent Reconstitution Solution. The Enzyme Reagent was reconstituted to a fill volume of 3.4 mL with an "Enzyme Reagent Reconstitution Solution" containing 50 mM HEPES, 1 mM EDTA, 10% (v/v) TRITON7 X-100 detergent, 120 mM KCl, and 20% (v/v) glycerol, adjusted to pH 7.0 with 4 M NaOH.

Probe Reagent. The "Probe Reagent" contained 100 mM succinic acid, 2% (w/v) lithium lauryl sulfate, 100 mM LiOH, 15 mM aldrithiol-2, 1.2 M LiCl, 20 mM EDTA, 3% (v/v) ethyl alcohol, 1 nM detection probe adjusted to pH 4.7 with 2M LiOH.

Selection Reagent. The "Selection Reagent" contained 600 mM boric acid, 182.5 mM NaOH, and 1% (v/v) TRITON® X-100 detergent, adjusted to pH 8.5 with 4 M NaOH.

Detection Reagents. The "Detection Reagents" were Detect Reagent I, which contained 1 mM nitric acid and 32 mM $H_2O_2$, 30% (v/v), and Detect Reagent II, which contained 1.0 M NaOH and 2% (w/v) ZWITTERGENT® 3-14 detergent.

Oil Reagent. The "Oil Reagent" was a silicone oil (United Chemical Technologies, Inc., Bristol, Pa.; Cat. No. PS038).

Example 1

Specificity of an Amplification Assay for
*Mycobacterium tuberculosis* Complex Organisms
Over Other Mycobacterial Organisms This experiment was conducted to determine the specificity of an amplification assay targeting 23S rRNA belonging to members of the TB complex in the presence of other mycobacterial species. As noted above, members of the TB complex include *M. africanum, M. bovis*, including the attenuated BCG vaccine strains, *M. microti* and *M. tuberculosis*. In the present experiment, the *M. microti* organisms did not grow and, therefore, there is no specificity data for this TB complex species. Phylogenetically, *M. celatum* is considered the most closely related to the TB complex of organisms and, therefore, an assay for detecting members of the TB complex should not detectably hybridize to nucleic acid derived from *M. celatum*.

The mycobacterial species of this experiment were cultured in accordance with standard microbiological techniques to obtain sufficient quantities of organisms for testing. See GABY E. PFYFFER ET AL., MANUAL OF CLINICAL MICROBIOLOGY, ch. 36 (Patrick R. Murray et al. eds., $8^{th}$ ed. 2003). For each species tested, a 1 µL loopful of cells (approximately $3 \times 10^9$ colony forming units) was transferred to a reaction tube of a Ten-Tube Unit (Gen-Probe, CA; Cat. No. TU0022) containing 250 µL of a 0.01% (v/v) lithium lauryl sulfate ("LLS") solution and 2,000 copies of an internal control ("IC") transcript. To limit interference by contaminating mycobacteria in a sample, the internal control was a non-competitive sequence derived from an HIV-1 nucleic acid (the detection region of the internal control was a scrambled HIV-1 sequence). Reaction tubes containing two replicates each of a *M. tuberculosis* rRNA positive control (2.5 fg/replicate) and a negative control (0.01% (v/v) LLS) were also prepared and tested.

To lyse cells and release targeted nucleic acids, 250 µL of the Specimen Dilution Buffer was added to the reaction tubes before the reaction tubes were covered with a sealing card (Gen-Probe; Cat. No. 2085), vortexed, and then incubated at 95° C. for 30 minutes. Each 250 µL aliquot of the Specimen Dilution Buffer contained 15 pmol of a TB complex capture probe, 5 pmol of a TB complex T7 promoter-primer, 4.4 pmol of an IC capture probe, and 8.0 pmol of an IC T7 promoter-primer. The TB complex capture probe had the sequence of SEQ ID NO:31 ggaaucacaauuguuuucuccuccutttaaaaaaaaaaa-aaaaaaaaaaaaaaaaaaaa, which consisted of a 5' target binding region (SEQ ID NO:32) made up of 2'-O-methyl ribonucleotides for binding to 23S rRNA of the TB complex organisms, a 3' oligo(dA)$_{30}$ immobilized probe binding region, and a 5'-ttt-3' spacer sequence interposed between the target binding portion and the immobilized probe binding region to make the capture probe more flexible for binding to oligo (dT)$_{14}$ immobilized on the magnetic particles. The IC capture probe had a 5' target binding region specific for the internal control and the same 3' immobilized probe binding region and spacer as the TB complex capture probe. The TB complex T7 promoter-primer was a forward (antisense) primer having the sequence of SEQ ID NO:33 aatttaatacgactcactatag ggagac-caggccacttccgctaacc, which consisted of a 3' target-binding portion (SEQ ID NO:21) for binding to 23S rRNA of the TB complex organisms and a 5' T7 promoter sequence (SEQ ID NO:29). The IC T7 promoter-primer was also a forward (antisense) primer having a 3' target-binding portion specific for the internal control and the same T7 promoter sequence as the TB complex T7 promoter-primer. Following the 95° C. incubation, the contents of the reaction tubes were allowed to cool at room temperature for 10 minutes, thereby permitting the target binding regions of the capture probes and the promoter-primers to hybridize to their respective targets, and for the immobilized probe binding regions (oligo(dA)$_{30}$) of the capture probes to bind to oligo(dT)$_{14}$ immobilized on the magnetic particles.

After the samples were cooled, a DTS® 400 Target Capture System (Gen-Probe; Cat. No. 5105) was used to isolate and wash the magnetic particles. The DTS® 400 Target Capture System has a test tube bay for positioning TTUs and applying a magnetic field thereto. The TTUs were placed in the test tube bay on the DTS® 400 Target Capture System for 5 minutes in the presence of the magnetic field to isolate the magnetic particles within the reaction tubes, after which the sample solutions were aspirated from the TTUs. Each reaction tube was then provided with 1 mL of the Wash Solution, covered with a sealing card and vortexed to resuspend the magnetic particles. The TTUs were returned to the test tube bay on the DTS® 400 Target Capture System and allowed to stand at room temperature for about 5 minutes before the Wash Solution was aspirated.

Following the target capture step, 75 µL of the reconstituted Amplification Reagent was added to each reaction tube. Each 75 µL aliquot of the reconstituted Amplification Reagent contained 15 pmol of the TB complex T7 promoter-primer, 15 pmol of a non-T7 TB complex primer, 8 pmol of the IC T7 promoter-primer, and 15 pmol of a non-T7 IC. Both of the non-T7 primers were reverse (sense) primers. The non-T7 TB complex primer had the base sequence of SEQ ID NO:25 and the non-T7 IC primer had a sequence contained within the internal control. The reaction tubes were then provided with 200 µL of the Oil Reagent, covered with a sealing card, and vortexed. To initiate amplification, 25 µL of the reconstituted Enzyme Reagent was added to each reaction tube, the reaction tubes were again covered with a sealing card, and the contents of the reaction tubes were gently mixed by hand. After mixing, the reaction tubes were incubated in a 42° C. water bath for 30 minutes.

For detection of TB complex and internal control amplification products, the reaction tubes were removed from the water bath and 100 µL of the Probe Reagent was added to each reaction tube. Each 100 µL contained 100 fmol of a TB complex detection probe, 2.5 pmol of a TB complex first helper probe (SEQ ID NO:5), 2.5 pmol of a TB complex second helper probe (SEQ ID NO:9), and 2 fmol of an IC detection probe was added. The TB complex detection probe had the base sequence of SEQ ID NO:1 and a standard AE label joined to the probe by means of a non-nucleotide linker positioned between nucleotides 13 and 14, reading 5' to 3'. The IC detection probe had an ortho-fluoro-AE label joined to the probe by means of a non-nucleotide linker. The reaction tubes were covered with a sealing card and vortexed before being incubated in a 62° C. water bath for 15 minutes to allow for hybridization of the probes to amplification products present in the reaction tubes. The reaction tubes were then removed from the water bath and allowed to cool at room temperature for 5 minutes before adding 250 µL of the Selection Reagent to each reaction tube. The reaction tubes were covered with a sealing card and vortexed before being incubated in a 62° C. water bath for 10 minutes to hydrolyze acridinium ester labels associated with unhybridized probe. The reaction tubes were then cooled at room temperature for 7 minutes before being analyzed in a LEADER® HC+Luminometer (Gen-Probe; Cat. No. 5201) equipped with automatic injection of Detection Reagent 1, followed by automatic injection of Detection Reagent 2.

The results are summarized in Table 1 below and indicate that the TB complex assay of this experiment amplified and detected TB complex-derived nucleic acid without cross-reacting with nucleic acid derived from other mycobacterial species. In this experiment, an internal control signal was considered positive if the RLU (relative light unit) value was between 30,000 and 299,999 RLU, and the TB complex assay signal was considered positive if RLU value was ≧300,000 RLU. The results set forth in Table 1 further show that the samples did not inhibit amplification of the internal control, and that the lysis procedure did not prevent amplification of the targeted sequences.

TABLE 1

Specificity of Amplification Assay for TB Complex Organisms Over Non-TB Complex Mycobacterial Organisms

| Mycobacterial Organism | ATCC Number | Combined Probes (RLU) |
|---|---|---|
| M. abcessus | 19977 | 105,929 |
| M. africanum | 25420 | 3,238,198 |
| M. asiaticum | 25276 | 74,624 |
| M. avium | 25291 | 91,042 |
| M. bovis | 19210 | 3,140,305 |
| M. bovis BCG | 35374 | 3,249,160 |
| M. celatum | 51130 | 104,160 |
| M. chelonae | 14472 | 102,643 |
| M. chelonae chelonae | 35752 | 102,268 |
| M. flavescens | 14474 | 95,497 |
| M. fortuitum | 6841 | 103,965 |
| M. gastri | 15754 | 104,267 |
| M. gordonae | 14470 | 77,905 |
| M intracellulare | 13950 | 63,543 |
| M. kamsasii | 12478 | 78,296 |
| M. malmoense | 29571 | 103,402 |
| M. marinum | 927 | 93,987 |
| M. scrofulaceum | 19981 | 98,773 |
| M. simiae | 25275 | 90,291 |
| M. smegmatis | 14468 | 102,800 |
| M. szulgai | 35799 | 109,171 |
| M. terrae | 15755 | 107,402 |
| M. tuberculosis H37Ra | 25177 | 3,250,601 |
| M. ulcerans | 19423 | 100,657 |
| M. xenopi | 19250 | 103,764 |
| Positive Control | 25177 | 3,445,956 |
| Negative Control | N/A | 2014 |

Example 2

Specificity of an Amplification Assay for *Mycobacterium tuberculosis* Complex Organisms Over Other Non-Mycobacterial Organisms This experiment evaluated the specificity of the TB complex assay of Example 1 in the presence of a variety of non-mycobacterial organisms. The organisms included in this experiment were selected for their relatedness to the TB complex organisms, to provide a cross-section of phylogeny, and/or because they are respiratory organisms. No internal control was included. Otherwise, the oligonucleotides, reagents and steps of this experiment were essentially the same as those described in Example 1. The results are set forth in Table 2 below and show that the TB complex assay of this experiment amplified and detected nucleic acid of the positive control and did not cross-react with nucleic acid derived from the non-mycobacterial species.

TABLE 2

Specificity of Amplification Assay for TB Complex Organisms Over Non-TB Complex Organisms

| Organism | ATCC Number | TB Complex Probe (RLU) |
|---|---|---|
| Actinomyces pyogenes | 19411 | 951 |
| Bordetella bronchiseptica | 10580 | 670 |
| Bordetella pertussis | 9797 | 650 |
| Candida albicans | 18804 | 73 |
| Corynebacterium aquaticum | 14665 | 725 |
| Corynebacterium diphtheriae | 11913 | 551 |
| Corynebacterium genitalium | 33030 | 609 |
| Corynebacterium haemolyticum | 9345 | 520 |
| Corynebacterium matruchotii | 33806 | 567 |
| Corynebacterium minitissimum | 23347 | 570 |
| Corynebacterium pseudodipthericum | 10700 | 603 |
| Corynebacterium pseudogenitalium | 33035 | 609 |
| Corynebacterium pseudotuberculosis | 19410 | 601 |
| Corynebacterium renale | 19412 | 603 |
| Corynebacterium striatum | 6940 | 609 |
| Eikenella corrodens | 23834 | 507 |
| Enterobacter aerogenes | 13048 | 632 |
| Enterococcus faecalis | 19433 | 579 |
| Enterococcus faecium | 19434 | 645 |
| Haemophilus influenzae | 19418 | 806 |
| Haemophilus parainfluenzae | 33392 | 910 |
| Klebsiella pneumoniae subsp. ozonae | 11296 | 641 |
| Klebsiella pneumoniae | 23357 | 628 |
| Legionella pneumophila | 33152 | 626 |
| Neisseria meningitidis | 13077 | 634 |
| Nocardia asteroides | 19247 | 641 |
| Nocardia brasiliensis | 19296 | 679 |
| Nocardia farcinica | 3318 | 653 |
| Nocardia otitidis-caviarum | 14629 | 641 |
| Peptostreptococcus magnus | 14955 | 607 |
| Pseudomonas aeruginosa | 25330 | 610 |
| Rhodococcus aichiensis | 33611 | 573 |
| Rhodococcus bronchialis | 25592 | 547 |
| Rhodococcus chubuensis | 33609 | 503 |
| Rhodococcus equi | 6939 | 594 |
| Rhodococcus obuensis | 33610 | 591 |
| Rhodococcus sputi | 29627 | 589 |
| Staphylococcus aureus | 12598 | 503 |
| Staphylococcus epidermidis | 12228 | 728 |
| Streptococcus pneumoniae | 6306 | 704 |
| Streptococcus pyogenes | 19615 | 537 |
| Positive Control | 25177 | 304,493 |
| Negative Control | N/A | 758 |

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A method for obtaining and initiating amplification of a target nucleic acid sequence from a mycobacterial organism present in a sample, the method comprising the steps of:
   a) exposing a sample to a lytic composition for about 15 minutes to at least, or about, 60 minutes under conditions sufficient to kill and lyse said organism that include a temperature of about 60° C. to at least, or about, 95° C., thereby releasing a target nucleic acid into a lysate, the lytic composition comprising a detergent, an amplification oligonucleotide for amplifying a target nucleic acid sequence contained in the target nucleic acid, a solid support comprising a plurality of magnetically charged particles or beads, and a capture probe for immobilizing the target nucleic acid on the solid support;
   b) forming a hybrid complex in the lysate, which hybrid complex comprises the capture probe, the target nucleic acid and the amplification oligonucleotide;
   c) immobilizing the hybrid complex on the solid support and removing components of the lysate which are not part of the hybrid complex formed in step b); and
   d) exposing the target nucleic acid to amplification conditions, such that the amplification oligonucleotide is enzymatically extended to form a complementary copy of the target nucleic acid sequence.

2. The method of claim 1, wherein the temperature of step b) is lower than the temperature of step a).

3. The method of claim 1, wherein the sample is exposed to the lytic composition for at least, or about, 15 minutes under conditions that include a temperature of at least, or about, 95° C.

4. The method of claim 1, wherein the amplification oligonucleotide comprises a promoter sequence which is recognized by an RNA polymerase.

5. The method of claim 1, wherein the detergent is a cationic detergent.

6. The method of claim 5, wherein the detergent is lithium lauryl sulfate.

7. The method of claim 5, wherein the detergent is present at a concentration of from about 0.1 to about 5% (v/v) in step a).

8. The method of claim 5, wherein the detergent is present at a concentration of from about 0.1 to about 3% (v/v) in step a).

9. The method of claim 5, wherein the detergent is present at a concentration of from about 0.1 to about 1.5% (v/v) in step a).

10. The method of claim 5, wherein the detergent is present at a concentration of from about 0.1 to about 0.3% (v/v) in step a).

11. The method of claim 1, wherein mechanical means are not used to lyse the organism.

12. The method of claim 1, wherein sonication is not used to lyse the organism.

13. The method of claim 1, wherein the salt concentration of steps a)-c) is from about 0.6 M to about 0.9 M.

14. The method of claim 1, wherein the sample is a respiratory sample.

15. The method of claim 14, wherein the respiratory sample is sputum.

16. The method of claim 1, where the mycobacterial organism is a *Mycobacterium tuberculosis* complex organism.

* * * * *